United States Patent
Messerly et al.

(10) Patent No.: US 12,213,746 B2
(45) Date of Patent: Feb. 4, 2025

(54) ULTRASOUND SYSTEM WITH TARGET AND MEDICAL INSTRUMENT AWARENESS

(71) Applicant: Bard Access Systems, Inc., Salt Lake City, UT (US)

(72) Inventors: Shayne Messerly, Kaysville, UT (US); Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/534,099

(22) Filed: Nov. 23, 2021

(65) Prior Publication Data
US 2022/0160434 A1 May 26, 2022

Related U.S. Application Data

(60) Provisional application No. 63/117,883, filed on Nov. 24, 2020.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 5/318* (2021.01); *A61B 8/0841* (2013.01);
(Continued)

(58) Field of Classification Search
CPC ......... A61B 34/20; A61B 5/062; A61B 5/318; A61B 8/0841; A61B 8/0891; A61B 2034/2063; G06N 20/10; G16H 30/20
See application file for complete search history.

(56) References Cited

U.S. PATENT DOCUMENTS

| 3,697,917 A | 10/1972 | Orth et al. |
| 5,148,809 A | 9/1992 | Biegeleisen-Knight et al. |

(Continued)

FOREIGN PATENT DOCUMENTS

| CN | 102871645 A | 1/2013 |
| CN | 105107067 B | 5/2018 |

(Continued)

OTHER PUBLICATIONS

M. Ikhsan, K. K. Tan, A. S. Putra, C. F. Kong, et al., "Automatic identification of blood vessel cross-section for central venous catheter placement using a cascading classifier," 39th Annual International Conference of the IEEE Engineering in Medicine and Biology Society (EMBC).pp. 1489-1492 (Year: 2017).*

(Continued)

*Primary Examiner* — Amal Aly Farag
(74) *Attorney, Agent, or Firm* — Rutan & Tucker LLP

(57) ABSTRACT

Blood vessel recognition and needle guidance systems, components, and methods thereof are disclosed. A console can be configured to instantiate a target recognition process for recognizing an anatomical target, such as a blood vessel, of a patient and a needle guidance process for guiding insertion of a needle into the anatomical target using ultrasound-imaging data received by the console. The system can perform target identification based on artificial intelligence (AI), which can be trained to recognize targets based on the ultrasound image. The ultrasound probe can be configured to provide to the console electrical signals corresponding to the ultrasound-imaging data. The ultrasound probe can include an array of transducers and, optionally, an array of magnetic sensors respectively configured to convert reflected ultrasound signals from the patient and magnetic signals from the needle, when magnetized, into the electrical signals.

17 Claims, 11 Drawing Sheets

(51) Int. Cl.
*A61B 5/318* (2021.01)
*A61B 8/08* (2006.01)
*G06N 20/10* (2019.01)
*G16H 30/20* (2018.01)

(52) U.S. Cl.
CPC .......... *A61B 8/0891* (2013.01); *G06N 20/10* (2019.01); *G16H 30/20* (2018.01); *A61B 2034/2063* (2016.02)

(56) References Cited

U.S. PATENT DOCUMENTS

| | | | |
|---|---|---|---|
| 5,181,513 A | 1/1993 | Touboul et al. | |
| 5,325,293 A | 6/1994 | Dorne | |
| 5,349,865 A | 9/1994 | Kavli et al. | |
| 5,441,052 A | 8/1995 | Miyajima | |
| 5,549,554 A | 8/1996 | Miraki | |
| 5,573,529 A | 11/1996 | Haak et al. | |
| 5,758,650 A | 6/1998 | Miller et al. | |
| 5,775,322 A | 7/1998 | Silverstein et al. | |
| 5,879,297 A | 3/1999 | Haynor et al. | |
| 5,897,503 A | 4/1999 | Lyon et al. | |
| 5,908,387 A | 6/1999 | LeFree et al. | |
| 5,967,984 A | 10/1999 | Chu et al. | |
| 5,970,119 A | 10/1999 | Hofmann | |
| 6,004,270 A | 12/1999 | Urbano et al. | |
| 6,019,724 A | 2/2000 | Gronningsaeter et al. | |
| 6,068,599 A | 5/2000 | Saito et al. | |
| 6,074,367 A | 6/2000 | Hubbell | |
| 6,129,668 A | 10/2000 | Haynor et al. | |
| 6,132,379 A | 10/2000 | Patacsil et al. | |
| 6,216,028 B1 | 4/2001 | Haynor et al. | |
| 6,233,476 B1 | 5/2001 | Strommer et al. | |
| 6,245,018 B1 | 6/2001 | Lee | |
| 6,263,230 B1 | 7/2001 | Haynor et al. | |
| 6,375,615 B1 | 4/2002 | Flaherty et al. | |
| 6,436,043 B2 | 8/2002 | Bonnefous | |
| 6,498,942 B1 | 12/2002 | Esenaliev et al. | |
| 6,503,205 B2 | 1/2003 | Manor et al. | |
| 6,508,769 B2 | 1/2003 | Bonnefous | |
| 6,511,458 B2 | 1/2003 | Milo et al. | |
| 6,524,249 B2 | 2/2003 | Moehring et al. | |
| 6,543,642 B1 | 4/2003 | Milliorn | |
| 6,554,771 B1 | 4/2003 | Buil et al. | |
| 6,592,520 B1 | 7/2003 | Peszynski et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,623,431 B1 | 9/2003 | Sakuma et al. | |
| 6,641,538 B2 | 11/2003 | Nakaya et al. | |
| 6,647,135 B2 | 11/2003 | Bonnefous | |
| 6,687,386 B1 | 2/2004 | Ito et al. | |
| 6,733,458 B1 | 5/2004 | Steins et al. | |
| 6,749,569 B1 | 6/2004 | Pellegretti | |
| 6,754,608 B2 | 6/2004 | Svanerudh et al. | |
| 6,755,789 B2 | 6/2004 | Stringer et al. | |
| 6,840,379 B2 | 1/2005 | Franks-Farah et al. | |
| 6,857,196 B2 | 2/2005 | Dalrymple | |
| 6,979,294 B1 | 12/2005 | Selzer et al. | |
| 7,074,187 B2 | 7/2006 | Selzer et al. | |
| 7,244,234 B2 | 7/2007 | Ridley et al. | |
| 7,359,554 B2 | 4/2008 | Klingensmith et al. | |
| 7,534,209 B2 | 5/2009 | Abend et al. | |
| 7,599,730 B2 | 10/2009 | Hunter et al. | |
| 7,637,870 B2 | 12/2009 | Flaherty et al. | |
| 7,681,579 B2 | 3/2010 | Schwartz | |
| 7,691,061 B2 | 4/2010 | Hirota | |
| 7,699,779 B2 | 4/2010 | Sasaki et al. | |
| 7,720,520 B2 | 5/2010 | Willis | |
| 7,727,153 B2 | 6/2010 | Fritz et al. | |
| 7,734,326 B2 | 6/2010 | Pedain et al. | |
| 7,831,449 B2 | 11/2010 | Ying et al. | |
| 7,905,837 B2 | 3/2011 | Suzuki | |
| 7,925,327 B2 | 4/2011 | Weese | |
| 7,927,278 B2 | 4/2011 | Selzer et al. | |
| 8,014,848 B2 | 9/2011 | Birkenbach et al. | |
| 8,038,619 B2 | 10/2011 | Steinbacher | |
| 8,060,181 B2 | 11/2011 | Rodriguez Ponce et al. | |
| 8,075,488 B2 | 12/2011 | Burton | |
| 8,090,427 B2 | 1/2012 | Eck et al. | |
| 8,105,239 B2 | 1/2012 | Specht | |
| 8,172,754 B2 | 5/2012 | Watanabe et al. | |
| 8,175,368 B2 | 5/2012 | Sathyanarayana | |
| 8,200,313 B1 | 6/2012 | Rambod et al. | |
| 8,211,023 B2 | 7/2012 | Swan et al. | |
| 8,228,347 B2 | 7/2012 | Beasley et al. | |
| 8,298,147 B2 | 10/2012 | Huennekens et al. | |
| 8,303,505 B2 | 11/2012 | Webler et al. | |
| 8,323,202 B2 | 12/2012 | Roschak et al. | |
| 8,328,727 B2 | 12/2012 | Miele et al. | |
| 8,388,541 B2 | 3/2013 | Messerly et al. | |
| 8,409,103 B2 | 4/2013 | Grunwald et al. | |
| 8,449,465 B2 | 5/2013 | Nair et al. | |
| 8,553,954 B2 | 10/2013 | Saikia | |
| 8,556,815 B2 | 10/2013 | Pelissier et al. | |
| 8,585,600 B2 | 11/2013 | Liu et al. | |
| 8,622,913 B2 | 1/2014 | Dentinger et al. | |
| 8,706,457 B2 | 4/2014 | Hart et al. | |
| 8,727,988 B2 | 5/2014 | Flaherty et al. | |
| 8,734,357 B2 | 5/2014 | Taylor | |
| 8,744,211 B2 | 6/2014 | Owen | |
| 8,754,865 B2 | 6/2014 | Merritt et al. | |
| 8,764,663 B2 | 7/2014 | Smok et al. | |
| 8,781,194 B2 | 7/2014 | Malek et al. | |
| 8,781,555 B2 | 7/2014 | Burnside et al. | |
| 8,790,263 B2 | 7/2014 | Randall et al. | |
| 8,849,382 B2 | 9/2014 | Cox et al. | |
| 8,939,908 B2 | 1/2015 | Suzuki et al. | |
| 8,961,420 B2 | 2/2015 | Zhang | |
| 9,022,940 B2 | 5/2015 | Meier | |
| 9,138,290 B2 | 9/2015 | Hadjicostis | |
| 9,199,082 B1 | 12/2015 | Yared et al. | |
| 9,204,858 B2 | 12/2015 | Pelissier et al. | |
| 9,220,477 B2 | 12/2015 | Urabe et al. | |
| 9,295,447 B2 | 3/2016 | Shah | |
| 9,320,493 B2 | 4/2016 | Visveshwara | |
| 9,357,980 B2 | 6/2016 | Toji et al. | |
| 9,364,171 B2 | 6/2016 | Harris et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,582,876 B2 | 2/2017 | Specht | |
| 9,610,061 B2 | 4/2017 | Ebbini et al. | |
| 9,636,031 B2 | 5/2017 | Cox | |
| 9,649,037 B2 | 5/2017 | Lowe et al. | |
| 9,649,048 B2 | 5/2017 | Cox et al. | |
| 9,702,969 B2 | 7/2017 | Hope Simpson et al. | |
| 9,715,757 B2 | 7/2017 | Ng et al. | |
| 9,717,415 B2 | 8/2017 | Cohen et al. | |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,861,337 B2 | 1/2018 | Patwardhan et al. | |
| 9,895,138 B2 | 2/2018 | Sasaki | |
| 9,913,605 B2 | 3/2018 | Harris et al. | |
| 9,949,720 B2 | 4/2018 | Southard et al. | |
| 10,043,272 B2 | 8/2018 | Forzoni et al. | |
| 10,449,330 B2 | 10/2019 | Newman et al. | |
| 10,524,691 B2 | 1/2020 | Newman et al. | |
| 10,751,509 B2 | 8/2020 | Misener | |
| 11,564,861 B1 | 1/2023 | Gaines | |
| 2002/0038088 A1 | 3/2002 | Imran et al. | |
| 2003/0047126 A1 | 3/2003 | Tomaschko | |
| 2003/0106825 A1 | 6/2003 | Molina et al. | |
| 2003/0120154 A1 | 6/2003 | Sauer et al. | |
| 2003/0125629 A1 | 7/2003 | Ustuner | |
| 2003/0135115 A1* | 7/2003 | Burdette | A61N 5/103 |
| | | | 600/437 |

(56) References Cited

U.S. PATENT DOCUMENTS

| | | |
|---|---|---|
| 2003/0149366 A1 | 8/2003 | Stringer et al. |
| 2004/0015080 A1 | 1/2004 | Kelly et al. |
| 2004/0055925 A1 | 3/2004 | Franks-Farah et al. |
| 2004/0197267 A1* | 10/2004 | Black ............... A61K 49/0041 424/9.6 |
| 2005/0000975 A1 | 1/2005 | Carco et al. |
| 2005/0049504 A1 | 3/2005 | Lo et al. |
| 2005/0075597 A1 | 4/2005 | Vournakis et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0004290 A1 | 1/2006 | Smith et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0047617 A1* | 3/2006 | Bacioiu ............... G06N 3/08 717/124 |
| 2006/0079781 A1 | 4/2006 | Germond-Rouet et al. |
| 2006/0184029 A1* | 8/2006 | Haim ............... A61B 8/0833 600/443 |
| 2006/0210130 A1 | 9/2006 | Germond-Rouet et al. |
| 2006/0241463 A1 | 10/2006 | Shau et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1* | 7/2007 | Timinger ............... A61B 90/36 606/1 |
| 2007/0199848 A1 | 8/2007 | Ellswood et al. |
| 2007/0239005 A1 | 10/2007 | Ogasawara |
| 2007/0239120 A1 | 10/2007 | Brock et al. |
| 2007/0249911 A1 | 10/2007 | Simon |
| 2007/0287886 A1* | 12/2007 | Saadat ............... A61B 5/6882 600/115 |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0269605 A1 | 10/2008 | Nakaya |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1 | 1/2009 | Steinbacher |
| 2009/0074280 A1* | 3/2009 | Lu ............... A61B 8/00 382/131 |
| 2009/0124903 A1 | 5/2009 | Osaka |
| 2009/0137887 A1 | 5/2009 | Shariati et al. |
| 2009/0137907 A1 | 5/2009 | Takimoto et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1* | 11/2009 | Boyden ............... A61B 5/412 600/407 |
| 2009/0306509 A1 | 12/2009 | Pedersen et al. |
| 2010/0010348 A1 | 1/2010 | Halmann |
| 2010/0168576 A1 | 7/2010 | Poland et al. |
| 2010/0211026 A2 | 8/2010 | Sheetz et al. |
| 2010/0249598 A1 | 9/2010 | Smith et al. |
| 2010/0286515 A1 | 11/2010 | Gravenstein et al. |
| 2010/0312121 A1 | 12/2010 | Guan |
| 2010/0324423 A1 | 12/2010 | El-Aklouk et al. |
| 2011/0002518 A1 | 1/2011 | Ziv-Ari et al. |
| 2011/0026796 A1 | 2/2011 | Hyun et al. |
| 2011/0071404 A1 | 3/2011 | Schmitt et al. |
| 2011/0074244 A1 | 3/2011 | Osawa |
| 2011/0087107 A1 | 4/2011 | Lindekugel et al. |
| 2011/0166451 A1 | 7/2011 | Blaivas et al. |
| 2011/0282188 A1* | 11/2011 | Burnside ............... A61B 34/25 600/424 |
| 2011/0295108 A1 | 12/2011 | Cox et al. |
| 2011/0313293 A1 | 12/2011 | Lindekugel et al. |
| 2012/0136242 A1* | 5/2012 | Qi ............... A61B 8/5223 604/95.01 |
| 2012/0136256 A1 | 5/2012 | Nozaki et al. |
| 2012/0165679 A1 | 6/2012 | Orome et al. |
| 2012/0179038 A1 | 7/2012 | Meurer et al. |
| 2012/0179042 A1 | 7/2012 | Fukumoto et al. |
| 2012/0179044 A1 | 7/2012 | Chiang et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1* | 4/2013 | Southard ............... C08G 61/125 600/424 |
| 2013/0131499 A1 | 5/2013 | Chan et al. |
| 2013/0131502 A1 | 5/2013 | Blaivas et al. |
| 2013/0144166 A1 | 6/2013 | Specht et al. |
| 2013/0150724 A1 | 6/2013 | Blaivas et al. |
| 2013/0188832 A1 | 7/2013 | Ma et al. |
| 2013/0197367 A1 | 8/2013 | Smok et al. |
| 2013/0218024 A1 | 8/2013 | Boctor et al. |
| 2013/0323700 A1* | 12/2013 | Samosky ............... G09B 23/30 434/262 |
| 2013/0338503 A1 | 12/2013 | Cohen et al. |
| 2013/0338508 A1 | 12/2013 | Nakamura et al. |
| 2013/0345566 A1 | 12/2013 | Weitzel et al. |
| 2014/0005530 A1 | 1/2014 | Liu et al. |
| 2014/0031694 A1 | 1/2014 | Solek |
| 2014/0066779 A1 | 3/2014 | Nakanishi |
| 2014/0073976 A1 | 3/2014 | Fonte et al. |
| 2014/0100440 A1 | 4/2014 | Cheline et al. |
| 2014/0114194 A1 | 4/2014 | Kanayama et al. |
| 2014/0170620 A1 | 6/2014 | Savitsky et al. |
| 2014/0180098 A1 | 6/2014 | Flaherty et al. |
| 2014/0180116 A1 | 6/2014 | Lindekugel et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1 | 9/2014 | Amble et al. |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2014/0357994 A1 | 12/2014 | Jin et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0141821 A1 | 5/2015 | Yoshikawa et al. |
| 2015/0190111 A1 | 7/2015 | Fry |
| 2015/0209003 A1 | 7/2015 | Halmann et al. |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0257735 A1 | 9/2015 | Ball et al. |
| 2015/0272448 A1 | 10/2015 | Fonte et al. |
| 2015/0282890 A1 | 10/2015 | Cohen et al. |
| 2015/0294497 A1 | 10/2015 | Ng et al. |
| 2015/0297097 A1 | 10/2015 | Matsubara et al. |
| 2015/0342572 A1 | 12/2015 | Tahmasebi Maraghoosh et al. |
| 2015/0359520 A1 | 12/2015 | Shan et al. |
| 2015/0359991 A1* | 12/2015 | Dunbar ............... A61B 8/4254 600/424 |
| 2016/0000367 A1 | 1/2016 | Lyon |
| 2016/0000399 A1 | 1/2016 | Halmann et al. |
| 2016/0026894 A1 | 1/2016 | Nagase |
| 2016/0029995 A1 | 2/2016 | Navratil et al. |
| 2016/0081674 A1 | 3/2016 | Bagwan et al. |
| 2016/0113517 A1 | 4/2016 | Lee et al. |
| 2016/0113699 A1 | 4/2016 | Sverdlik et al. |
| 2016/0120607 A1 | 5/2016 | Sorotzkin et al. |
| 2016/0157831 A1* | 6/2016 | Kang ............... A61B 8/5276 600/443 |
| 2016/0166232 A1 | 6/2016 | Merritt |
| 2016/0202053 A1 | 7/2016 | Walker et al. |
| 2016/0211045 A1 | 7/2016 | Jeon et al. |
| 2016/0213398 A1 | 7/2016 | Liu |
| 2016/0220124 A1 | 8/2016 | Grady et al. |

(56) References Cited

U.S. PATENT DOCUMENTS

| | | |
|---|---|---|
| 2016/0259992 A1 | 9/2016 | Knodt et al. |
| 2016/0278869 A1 | 9/2016 | Grunwald |
| 2016/0287214 A1 | 10/2016 | Ralovich et al. |
| 2016/0296208 A1 | 10/2016 | Sethuraman et al. |
| 2016/0374644 A1 | 12/2016 | Mauldin, Jr. et al. |
| 2017/0014105 A1 | 1/2017 | Chono |
| 2017/0020561 A1 | 1/2017 | Cox et al. |
| 2017/0079548 A1 | 3/2017 | Silverstein et al. |
| 2017/0103534 A1 | 4/2017 | Park et al. |
| 2017/0143312 A1 | 5/2017 | Hedlund et al. |
| 2017/0164923 A1 | 6/2017 | Matsumoto |
| 2017/0172666 A1 | 6/2017 | Govari et al. |
| 2017/0215842 A1 | 8/2017 | Ryu et al. |
| 2017/0252004 A1 | 9/2017 | Broad et al. |
| 2017/0258522 A1 | 9/2017 | Goshgarian et al. |
| 2017/0328751 A1 | 11/2017 | Lemke |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0235649 A1 | 8/2018 | Elkadi |
| 2018/0235709 A1 | 8/2018 | Donhowe et al. |
| 2018/0289927 A1 | 10/2018 | Messerly |
| 2018/0296185 A1 | 10/2018 | Cox et al. |
| 2018/0310955 A1* | 11/2018 | Lindekugel ............ A61B 90/98 |
| 2018/0333135 A1 | 11/2018 | Kim et al. |
| 2018/0344293 A1 | 12/2018 | Raju et al. |
| 2019/0060001 A1* | 2/2019 | Kohli .................... A61B 34/20 |
| 2019/0060014 A1 | 2/2019 | Hazelton et al. |
| 2019/0090855 A1 | 3/2019 | Kobayashi et al. |
| 2019/0125210 A1* | 5/2019 | Govari ................ A61B 5/6852 |
| 2019/0200951 A1 | 7/2019 | Meier |
| 2019/0239848 A1 | 8/2019 | Bedi et al. |
| 2019/0239850 A1 | 8/2019 | Dalvin et al. |
| 2019/0307419 A1 | 10/2019 | Durfee |
| 2019/0307515 A1 | 10/2019 | Naito et al. |
| 2019/0365347 A1 | 12/2019 | Abe |
| 2019/0365348 A1 | 12/2019 | Toume et al. |
| 2019/0365354 A1 | 12/2019 | Du |
| 2020/0069929 A1 | 3/2020 | Mason et al. |
| 2020/0113540 A1 | 4/2020 | Gijsbers et al. |
| 2020/0163654 A1 | 5/2020 | Satir et al. |
| 2020/0200900 A1 | 6/2020 | Asami et al. |
| 2020/0229795 A1 | 7/2020 | Tadross et al. |
| 2020/0230391 A1* | 7/2020 | Burkholz ............... A61B 90/37 |
| 2020/0237403 A1 | 7/2020 | Southard et al. |
| 2020/0281563 A1 | 9/2020 | Muller et al. |
| 2020/0359990 A1 | 11/2020 | Poland et al. |
| 2020/0390416 A1 | 12/2020 | Swan et al. |
| 2021/0059639 A1 | 3/2021 | Howell |
| 2021/0077058 A1 | 3/2021 | Mashood et al. |
| 2021/0137492 A1 | 5/2021 | Imai |
| 2021/0146167 A1 | 5/2021 | Barthe et al. |
| 2021/0161510 A1 | 6/2021 | Sasaki et al. |
| 2021/0186467 A1 | 6/2021 | Urabe et al. |
| 2021/0212668 A1 | 7/2021 | Li et al. |
| 2021/0267569 A1 | 9/2021 | Yamamoto |
| 2021/0267570 A1 | 9/2021 | Ulman et al. |
| 2021/0295048 A1 | 9/2021 | Buras et al. |
| 2021/0315538 A1 | 10/2021 | Brandl et al. |
| 2021/0373602 A1 | 12/2021 | Min |
| 2021/0378627 A1 | 12/2021 | Yarmush et al. |
| 2022/0039777 A1 | 2/2022 | Durfee |
| 2022/0039829 A1 | 2/2022 | Zijlstra et al. |
| 2022/0071593 A1 | 3/2022 | Tran |
| 2022/0096053 A1 | 3/2022 | Sethuraman et al. |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0168050 A1 | 6/2022 | Sowards et al. |
| 2022/0172354 A1 | 6/2022 | Misener et al. |
| 2022/0296303 A1 | 9/2022 | McLeod et al. |
| 2022/0304652 A1 | 9/2022 | Peterson et al. |
| 2022/0330922 A1 | 10/2022 | Sowards et al. |
| 2022/0334251 A1 | 10/2022 | Sowards et al. |
| 2022/0361840 A1 | 11/2022 | Matsumoto et al. |
| 2023/0048327 A1 | 2/2023 | Lampe et al. |
| 2023/0107629 A1 | 4/2023 | Sowards et al. |
| 2023/0132148 A1 | 4/2023 | Sowards et al. |
| 2023/0135562 A1 | 5/2023 | Misener et al. |
| 2023/0138970 A1 | 5/2023 | Sowards et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0338010 A1 | 10/2023 | Sturm |
| 2023/0371928 A1 | 11/2023 | Rajguru et al. |
| 2023/0397900 A1 | 12/2023 | Prince |
| 2024/0065673 A1 | 2/2024 | Sowards et al. |
| 2024/0307024 A1 | 9/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 2823766 A1 | 1/2015 |
| EP | 3181083 A1 | 6/2017 |
| EP | 3870059 | 9/2021 |
| JP | 2000271136 A | 10/2000 |
| JP | 2007222291 A | 9/2007 |
| JP | 2014150928 A | 8/2014 |
| JP | 2018175547 A | 11/2018 |
| KR | 20180070878 A | 6/2018 |
| KR | 102176196 B1 | 11/2020 |
| WO | 2004082749 A2 | 9/2004 |
| WO | 2007115174 A2 | 10/2007 |
| WO | 2010029521 A2 | 3/2010 |
| WO | 2010076808 A1 | 7/2010 |
| WO | 2013059714 A1 | 4/2013 |
| WO | 2014/115150 A1 | 7/2014 |
| WO | 2015/017270 A1 | 2/2015 |
| WO | 2016081023 A1 | 5/2016 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020067897 A1 | 4/2020 |
| WO | 2020083660 A1 | 4/2020 |
| WO | 2020/186198 A1 | 9/2020 |
| WO | 2021123905 A2 | 6/2021 |
| WO | 2021198226 A1 | 10/2021 |
| WO | 2022/072727 A2 | 4/2022 |
| WO | 2022/081904 A1 | 4/2022 |
| WO | 2022/119853 A1 | 6/2022 |
| WO | 2022115479 A1 | 6/2022 |
| WO | 2022119856 A1 | 6/2022 |
| WO | 2022221703 A1 | 10/2022 |
| WO | 2022221714 A1 | 10/2022 |
| WO | 2023059512 A1 | 4/2023 |
| WO | 2023076268 A1 | 5/2023 |
| WO | 2023081220 A1 | 5/2023 |
| WO | 2023081223 A1 | 5/2023 |
| WO | 2023091424 A1 | 5/2023 |
| WO | 2023167866 A1 | 9/2023 |
| WO | 2023177718 A1 | 9/2023 |
| WO | 2024044277 A1 | 2/2024 |

OTHER PUBLICATIONS

U.S. Appl. No. 17/020,476, filed Sep. 14, 2020 Advisory Action dated Aug. 19, 2022.

(56) References Cited

OTHER PUBLICATIONS

U.S. Appl. No. 17/020,476, filed Sep. 14, 2020 Non-Final Office Action dated Sep. 23, 2022.
U.S. Appl. No. 17/471,015, filed Sep. 9, 2021 Non-Final Office Action dated Aug. 16, 2022.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
PCT/US2021/045218 filed Aug. 9, 2021 International Search Report and Written Opinion dated Nov. 23, 2021.
PCT/US2021/049123 filed Sep. 3, 2021 International Search Report and Written Opinion dated Feb. 4, 2022.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
U.S. Appl. No. 15/951,903, filed Apr. 12, 2018 Board Decision dated Apr. 20, 2022.
U.S. Appl. No. 17/020,476, filed Sep. 14, 2020 Non-Final Office Action dated Feb. 9, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US12/61182 International Seach Report and Written Opinion dated Mar. 11, 2013.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2022/025082 filed Apr. 15, 2022 International Search Report and Written Opinion dated Jul. 11, 2022.
PCT/US2022/025097 filed Apr. 15, 2022 International Search Report and Written Opinion dated Jul. 8, 2022.
U.S. Appl. No. 17/020,476, filed Sep. 14, 2020 Final Office Action dated Jun. 9, 2022.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022/049983 filed Nov. 15, 2022 International Search Report and Written Opinion dated Mar. 29, 2023.
PCT/US2022047727 filed Oct. 25, 2022 International Search Report and Written Opinion dated Jan. 25, 2023.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Final Office Action dated Jan. 5, 2023.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. Appl. No. 17/471,015, filed Sep. 9, 2021 Non-Final Office Action dated Mar. 30, 2023.
U.S. Appl. No. 17/538,911, filed Nov. 30, 2021 Non-Final Office Action dated Mar. 2, 2023.
U.S. Appl. No. 17/684,180, filed Mar. 1, 2022 Restriction Requirement dated May 19, 2023.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/471,015, filed Sep. 9, 2021 Final Office Action dated Oct. 12, 2023.
U.S. Appl. No. 17/538,911, filed Nov. 30, 2021 Advisory Action dated Nov. 22, 2023.
U.S. Appl. No. 17/722,151, filed Apr. 15, 2022 Final Office Action dated Nov. 6, 2023.
U.S. Appl. No. 17/894,460, filed Aug. 24, 2022 Non-Final Office Action dated Nov. 6, 2023.
U.S. Appl. No. 17/468,318, filed Sep. 7, 2021 Notice of Allowance dated Jan. 18, 2024.
U.S. Appl. No. 17/471,015, filed Sep. 9, 2021 Advisory Action dated Feb. 2, 2024.
U.S. Appl. No. 17/471,015, filed Sep. 9, 2021 Non-Final Office Action dated Mar. 28, 2024.
U.S. Appl. No. 17/538,911, filed Nov. 30, 2021 Notice of Allowance dated Mar. 14, 2024.
U.S. Appl. No. 17/538,943, filed Nov. 30, 2021 Non-Final Office Action dated Jan. 30, 2024.
U.S. Appl. No. 17/684,180, filed Mar. 1, 2022 Advisory Action dated Apr. 4, 2024.
U.S. Appl. No. 17/684,180, filed Mar. 1, 2022 Final Office Action dated Jan. 18, 2024.
U.S. Appl. No. 17/684,180, filed Mar. 1, 2022 Non-Final Office Action dated May 8, 2024.
U.S. Appl. No. 17/722,111, filed Apr. 15, 2022 Non-Final Office Action dated Dec. 22, 2023.
U.S. Appl. No. 17/722,151, filed Apr. 15, 2022 Advisory Action dated Jan. 2, 2024.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/894,460, filed Aug. 24, 2022 Final Office Action dated Jan. 31, 2024.

(56) References Cited

OTHER PUBLICATIONS

U.S. Appl. No. 17/979,564, filed Nov. 2, 2022 Non-Final Office Action dated Jun. 5, 2024.
U.S. Appl. No. 18/238,281, filed Aug. 25, 2023 Non-Final Office Action dated Mar. 22, 2024.
EP 20866520.8 filed Apr. 5, 2022 Extended European Search Report dated Aug. 22, 2023.
U.S. Appl. No. 17/468,318, filed Sep. 7, 2021 Final Office Action dated Sep. 8, 2023.
U.S. Appl. No. 17/538,911, filed Nov. 30, 2021 Final Office Action dated Sep. 13, 2023.
U.S. Appl. No. 17/684,180, filed Mar. 1, 2022 Non-Final Office Action dated Jul. 28, 2023.
U.S. Appl. No. 17/722,151, filed Apr. 15, 2022 Non-Final Office Action dated Sep. 7, 2023.
Thermographic venous blood flow characterization with external cooling stimulation (Year: 2018).
U.S. Appl. No. 17/538,943, filed Nov. 30, 2021 Notice of Allowance dated Aug. 14, 2024.
U.S. Appl. No. 17/684,180 filed Mar. 1, 2022 Final Office Action dated Sep. 23, 2024.
U.S. Appl. No. 17/722,111, filed Apr. 15, 2022 Final Office Action dated Jul. 12, 2024.
U.S. Appl. No. 17/722,151 filed Apr. 15, 2022 Final Office Action dated Sep. 20, 2024.
U.S. Appl. No. 17/894,460, filed Aug. 24, 2022 Non-Final Office Action dated Sep. 25, 2024.
U.S. Appl. No. 17/957,562, filed Sep. 30, 2022 Non-Final Office Action dated Jun. 20, 2024.
U.S. Appl. No. 17/979,601, filed Nov. 2, 2022 Non-Final Office Action dated Aug. 20, 2024.
U.S. Appl. No. 17/987,698, filed Nov. 15, 2022 Non-Final Office Action dated Sep. 20, 2024.
U.S. Appl. No. 18/238,281, filed Aug. 25, 2023 Notice of Allowance dated Jul. 16, 2024.
PCT/US2024/037647 filed Jul. 11, 2024 International Search Report and Written Opinion dated Oct. 16, 2024.
U.S. Appl. No. 17/471,015, filed Sep. 9, 2021 Notice of Allowance dated Oct. 29, 2024.
U.S. Appl. No. 17/722,111 filed Apr. 15, 2022 Advisory Action dated Oct. 23, 2024.
U.S. Appl. No. 17/957,562, filed Sep. 30, 2022 Final Office Action dated Nov. 27, 2024.
U.S. Appl. No. 17/979,564, filed Nov. 2, 2022 Final Office Action dated Oct. 18, 2024.
U.S. Appl. No. 18/113,003, filed Feb. 22, 2023 Non-Final Office Action dated Nov. 27, 2024.

\* cited by examiner

ULTRASOUND SYSTEM WITH TARGET AND MEDICAL INSTRUMENT AWARENESS

PRIORITY

This application claims the benefit of priority to U.S. Patent Application No. 63/117,883, filed Nov. 24, 2020, which is incorporated by reference in its entirety into this application.

SUMMARY

Briefly summarized, embodiments disclosed herein are directed to systems, methods and apparatuses for ultrasound target identification and medical instrument tracking. One potential problem that arises with ultrasound imaging during catheter insertion is identifying the proper targets. For example, challenges can include differentiating veins vs. arteries, finding a blood vessel suitable for catheter insertion, or finding a particular blood vessel. Locating the correct targets may consume clinical time and resources, and errors could cause potentially dangerous complications.

A second potential problem is locating and guiding the needle tip, particularly in its approach to the target blood vessel. For example, when inserting a peripherally inserted central catheter (PICC), the needle must be guided over a large distance from its peripheral insertion site through a vein or artery to the target, and it can be challenging to track or estimate correctly the needle's position. Moreover, the target may often be an essential, central blood vessel, such as the superior vena cava (SVC) or the cavoatrial junction (CAJ) thereof. Accordingly, it can be important to know the location and orientation of the needle precisely, in order to target the catheter insertion in a minimally invasive way and with the least risk of harm.

Other potential problems include navigation of the catheter tip, e.g., a PICC tip, during insertion, and confirmation of the tip location following insertion. In particular, it is very important to track the location of a PICC, central venous catheter (CVC), another catheter, or another medical device, in order to perform implantation minimally invasively and with minimal risk. It is likewise crucial to confirm that a medical device, such as a PICC, has been implanted in the correct target, such as the SVC. However, some methods for tip tracking and confirmation require fluoroscopy or X-ray exposure, and may also require exposure to harmful contrast media.

Disclosed herein is a target recognition and needle guidance system. The target recognition and needle guidance system comprises a console including memory and a processor, and an ultrasound probe. The console is configured to instantiate a target recognition process for recognizing an anatomical target of a patient, by applying an artificial intelligence model to features of candidate targets in ultrasound-imaging data to determine a recognition score. The console is further configured to instantiate a needle guidance process for guiding insertion of a needle into the anatomical target using the ultrasound-imaging data received by the console. The ultrasound probe is configured to provide to the console electrical signals corresponding to the ultrasound-imaging data. The ultrasound probe includes an array of transducers (optionally piezoelectric) configured to convert reflected ultrasound signals from the patient into an ultrasound-imaging portion of the electrical signals.

In some embodiments, the artificial intelligence model includes a supervised learning model trained based on previously-identified training targets.

In some embodiments, the recognition score comprises a probability or confidence level associated with a classification of the candidate targets in the ultrasound-imaging data.

In some embodiments, the artificial intelligence comprises one or more of the following supervised learning methods: logistic regression; other linear classifiers; support vector machines; quadratic classifiers; kernel estimation; decision trees; neural networks; or learning vector quantization.

In some embodiments, the artificial intelligence model includes the logistic regression, and the score is determined as a weighted sum of the features of the candidate targets.

In some embodiments, the artificial intelligence model includes the neural network, and the score is determined based on one or more nonlinear activation functions of the features of the candidate targets.

In some embodiments, the supervised learning model is trained by iteratively minimizing an error, for classifications predicted by a candidate model compared to actual classifications of the previously-identified training targets.

In some embodiments, the anatomical target comprises a blood vessel.

In some embodiments, the blood vessel comprises a superior vena cava.

In some embodiments, the ultrasound probe provides a first ultrasound image prior to the insertion of the needle. The artificial intelligence model is based in part on a trajectory of the needle.

In some embodiments, the features of the ultrasound-imaging data include one or more of the following features: a shape of a candidate blood vessel of the candidate targets in the ultrasound-imaging data; a size of the candidate blood vessel; a number of branches of the candidate blood vessel; or a complexity of branches of the candidate blood vessel.

In some embodiments, recognizing the anatomical target comprises one or more of: providing identifying information characterizing one or more potential targets to a user; suggesting the one or more potential targets for a selection by the user; or selecting a target of the one or more potential targets.

In some embodiments, recognizing the anatomical target comprises providing identifying information characterizing one or more potential targets to a user. The identifying information comprises a predicted classification of the one or more potential targets and a confidence level associated with the classification.

In some embodiments, the target recognition and needle guidance system further comprises a display screen configured for graphically guiding the insertion of the needle into the anatomical target of the patient.

In some embodiments, a catheter is disposed within the needle. The catheter is implanted into the anatomical target following the insertion of the needle.

In some embodiments, the target recognition and needle guidance system further includes a catheter magnetic sensor or a catheter light detector. The catheter magnetic sensor can be configured to provide to the console electrical signals corresponding to magnetic information about the catheter. The catheter light detector can be configured to provide to the console electrical signals corresponding to optical information about the catheter. The processor is further configured to instantiate a magnetic catheter tip tracking process based on the catheter magnetic information or an optical catheter tip tracking process based on the catheter optical information.

In some embodiments, the target recognition and needle guidance system further includes one or more electrocardiography probes configured to provide to the console electrical signals corresponding to electrocardiography information. The processor is further configured to instantiate a catheter tip placement confirmation process based on the electrocardiography information.

In some embodiments, the anatomical target comprises a biopsy target, a nerve to be blocked, or an abscess to be drained.

In some embodiments, the system further comprises a needle magnetizer incorporated into the console configured to magnetize a needle to obtain a magnetized needle.

In some embodiments, the needle guidance process for guiding insertion of the magnetized needle into the anatomical target uses a combination of the ultrasound-imaging data and magnetic-field data received by the console.

In some embodiments, the ultrasound probe is configured to provide to the console the magnetic-field data, the ultrasound probe further including an array of magnetic sensors configured to convert magnetic signals from the magnetized needle into a magnetic-field portion of the electrical signals.

Also disclosed herein is a method of a target recognition and needle guidance system. The method includes, in some embodiments, instantiating in memory of a console a target recognition process and a needle guidance process. The target recognition process can be for recognizing an anatomical target of a patient, by applying an artificial intelligence model to features of candidate targets in ultrasound-imaging data to determine a recognition score. The needle guidance process can be for guiding insertion of a needle into the anatomical target using the ultrasound-imaging data received by the console. The method further includes loading the ultrasound-imaging data in the memory, the ultrasound-imaging data corresponding to electrical signals received from an ultrasound probe. The method further includes processing the ultrasound-imaging data with a processor of the console according to the target recognition process and the needle guidance process. The method further includes guiding the insertion of the needle, according to the needle guidance process, into the anatomical target of the patient.

Also disclosed herein is a method of a target recognition and needle guidance system. The method includes, in some embodiments, obtaining a needle. The method further includes imaging an anatomical region of a patient with an ultrasound probe to produce ultrasound-imaging data. The method further includes recognizing, by the console, an anatomical target of the anatomical region of the patient, by applying an artificial intelligence model to features of candidate targets in ultrasound-imaging data to determine a recognition score. The method further includes orienting the needle for insertion into the anatomical target of the patient while imaging the anatomical region with the ultrasound probe. The method further includes inserting the needle into the anatomical target of the anatomical region in accordance with guidance provided by a needle guidance process instantiated by the console upon processing a combination of the ultrasound-imaging data.

In some embodiments, a catheter is disposed within the needle. The method further comprises implanting the catheter into the anatomical target following the insertion of the needle. In some embodiments, the needle guidance process for guiding insertion of a magnetized needle into the anatomical target uses a combination of the ultrasound-imaging data and magnetic-field data received by the console.

In some embodiments, the ultrasound probe is configured to provide to the console the magnetic-field data, the ultrasound probe further including an array of magnetic sensors configured to convert magnetic signals from a magnetized needle into a magnetic-field portion of the electrical signals.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1:
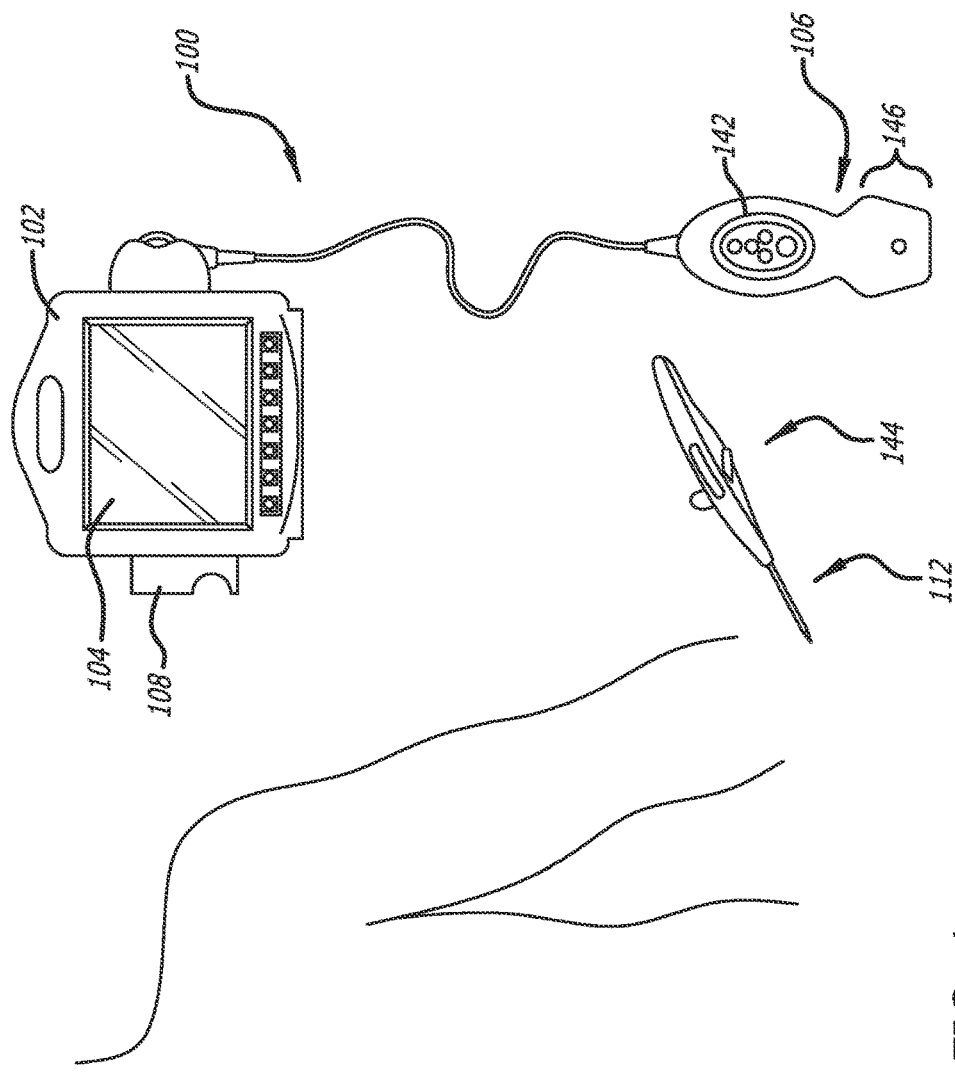
FIG. 1 illustrates an example ultrasound probe and needle guidance system with a patient, according to some embodiments.
Figure 1:
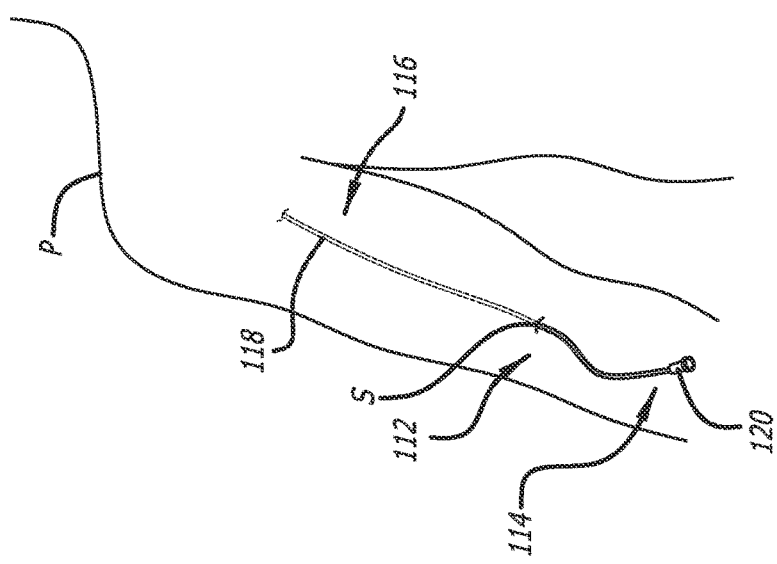

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Disclosed herein is a system, apparatus and method directed to an ultrasound probe, target identification system, and needle guidance system. One frequent challenge in procedures and therapies utilizing ultrasound imaging, such as catheter insertion, biopsy, nerve blocks, or drainage, is identifying the proper targets. A second challenge is locating and guiding a needle tip, particularly in its approach to a target blood vessel. Additional challenges can include navigation of a catheter tip, such as a peripherally inserted central catheter (PICC) tip, during insertion in the target, and confirmation of the tip location following insertion.

FIG. 1 illustrates an example ultrasound probe 106 included within a needle guidance system 100 with a patient P, according to some embodiments. System 100 performs ultrasound imaging of an insertion target, in this example a vasculature of patient P, together with magnetic needle guidance. The needle guidance system 100 can have a variety of uses, including placement of needles in preparation for inserting the catheter 112 or other medical components into a body of a patient. In this example, a clinician employs ultrasound probe 106 and needle guidance system 100 while performing a procedure to place a catheter 112 into a vasculature of the patient P through a skin insertion site S. Together, the ultrasound imaging and needle guidance functionalities enable the clinician to guide the needle accurately to its intended target.

However, there remains a need for assistance identifying the insertion target efficiently and accurately. In particular, there remains a need to reduce target identification errors that could lead to dangerous complications for the patient, while also reducing the costs and clinical time necessary to locate, identify, and insert the needle into the target. The system and methods disclosed herein below can address these needs.

FIG. 1 further depicts a needle-based device, namely a catheter-insertion device 144, used to gain initial access to the vasculature of the patient P via the insertion site S to deploy the catheter 112. Placement of a needle into a vasculature at the insertion site S is typically performed prior to insertion of the catheter 112. The catheter 112 generally includes a proximal portion 114 that remains exterior to the patient and a distal portion 116 that resides within the patient P's vasculature after placement is complete. The needle guidance system 100 is employed to ultimately position a distal tip 118 of the catheter 112 in a desired position within the vasculature. The proximal portion 114 of the catheter 112 further includes a Luer connector 120 configured to operably connect the catheter 112 with one or more other medical devices or systems.

The needle of the catheter-insertion device is configured to cooperate with the needle guidance system 100 in enabling the needle guidance system 100 to detect the position, orientation, and advancement of the needle during an ultrasound-based placement procedure. In some examples, other needles or medical devices may also be magnetized and used with the needle guidance system 100.

The display screen 104 is integrated into the console 102 and can display information to the clinician during the placement procedure, such as an ultrasound image of the targeted internal body portion obtained by ultrasound probe 106. In particular, the needle guidance process of the needle guidance system 100 can graphically guide insertion of a needle into the target by way of the display screen 104.

Figure 2:
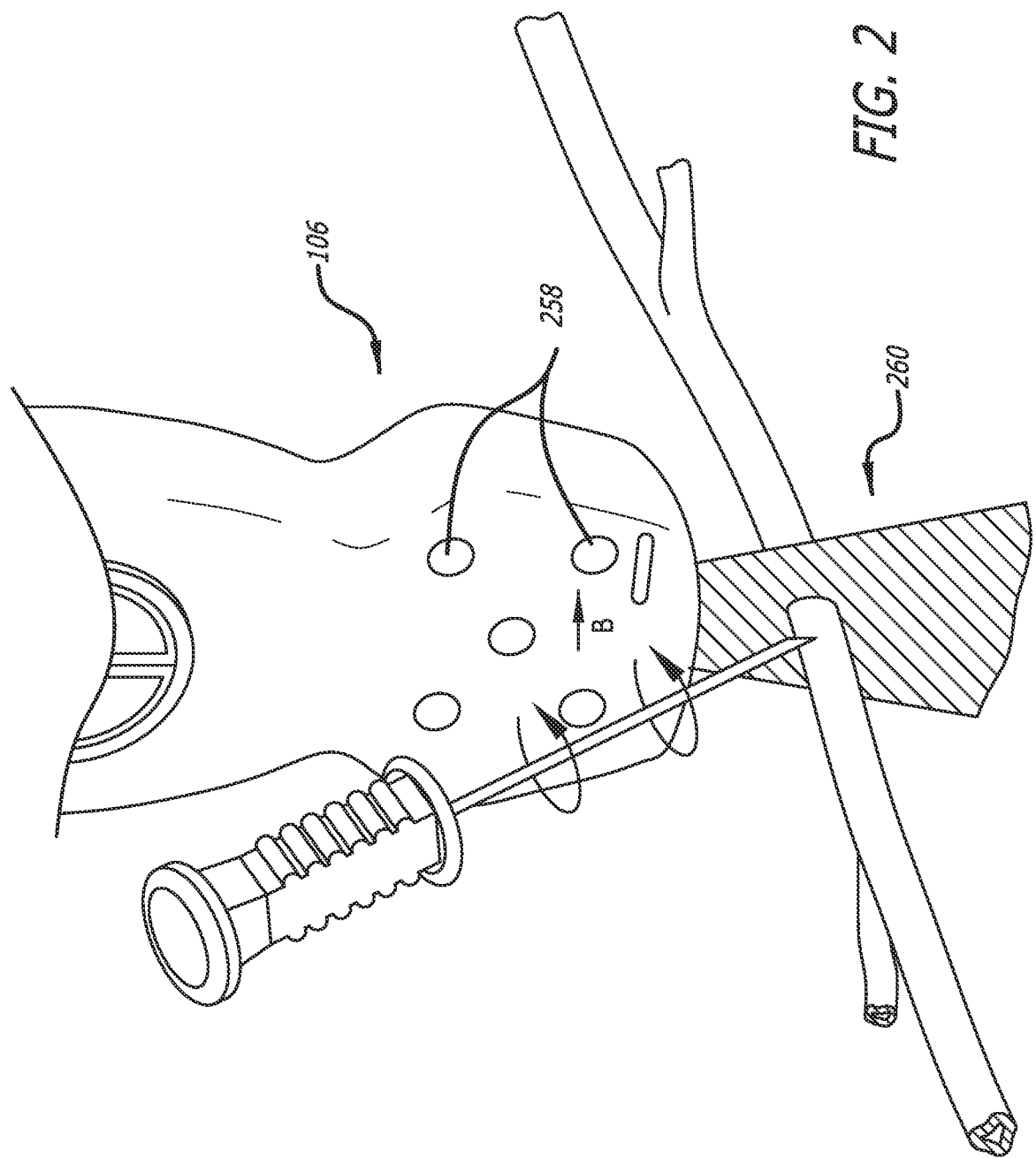
FIG. 2 illustrates insertion of a needle into a blood vessel using an ultrasound probe and needle guidance system, according to some embodiments.

FIG. 2 illustrates insertion of a needle into a blood vessel using an ultrasound probe 106 and needle guidance system, in accordance with some embodiments. The ultrasound probe 106 includes a sensor array for detecting the position, orientation, and movement of a needle during ultrasound imaging procedures. The sensor array includes a number of magnetic sensors 258 embedded within or included on the housing of the ultrasound probe 106. The magnetic sensors 258 detect a magnetic field or magnetic signals associated with the needle when the needle is magnetized and in proximity to the sensor array. Sensors 258 also convert the magnetic signals from the magnetized needle into a magnetic-field portion of the foregoing electrical signals to the console 102. (See the illustrated magnetic field B of the needle.) Accordingly, the sensor array enables the needle guidance system 100 to track a magnetized needle or the like.

Though illustrated in this example as magnetic sensors, sensors 258 may be sensors of other types and configurations. Also, in some examples, the magnetic sensors 258 of the sensor array can be included in a component separate from the ultrasound probe 106, such as a separate handheld device. In some embodiments, the magnetic sensors 258 are disposed in an annular configuration about the head 146 of the ultrasound probe 106, though it is appreciated that the magnetic sensors 258 can be arranged in other configurations, such as in an arched, planar, or semi-circular arrangement.

Five magnetic sensors 258 are included in the sensor array so as to enable detection of a needle three spatial dimensions (i.e., X, Y, Z coordinate space), as well as the pitch and yaw orientation of the needle itself. More generally, the number, size, type, and placement of the magnetic sensors 258 of the sensor array may vary from what is explicitly shown here.

A needle of a magnetizable material enables the needle to be magnetized by the magnetizer 108 and later be tracked by the needle guidance system 100 when the needle is percutaneously inserted into a body of a patient (e.g., the body of the patient P) during a procedure to insert the needle or an associated medical device (e.g., the catheter 112 of the catheter-insertion device 144) into the body of the patient P. For example, the needle may be composed of a stainless steel such as SS 304 stainless steel, or of some other suitable needle material that is capable of being magnetized, and is not limited by the present disclosure. The needle material may be ferromagnetic or paramagnetic. Accordingly, the needle can produce a magnetic field or signals detectable by the sensor array of the ultrasound probe 106 so as to enable the location, orientation, and movement of the needle to be tracked by the needle guidance system 100.

Needle guidance system 100 and magnetic sensors 258 are described further in US 2021/0169585, which is incorporated by reference in its entirety into this application.

In addition to tracking the location of the insertion needle, it also can be useful to track a medical device, such as the tip and/or stylet of a PICC, central venous catheter (CVC), or other catheter, during insertion. For example, such tip tracking can improve the accuracy and efficiency of catheter placement, improve patient outcomes, and reduce the risk of complications or injuries. Accordingly, in some examples, the system can use passive magnetic catheter tip tracking to locate and/or track tips of medical devices like PICCs, catheters, and/or stylets, and can thereby determine where such tips are located in relation to their target anatomical structures. This will be discussed further in the example of FIG. 6A below. In some cases, magnetic and electromagnetic means for tracking the tips of the medical devices are prone to interference. Accordingly, optical tip-tracking methods can also be used.

Figure 3:
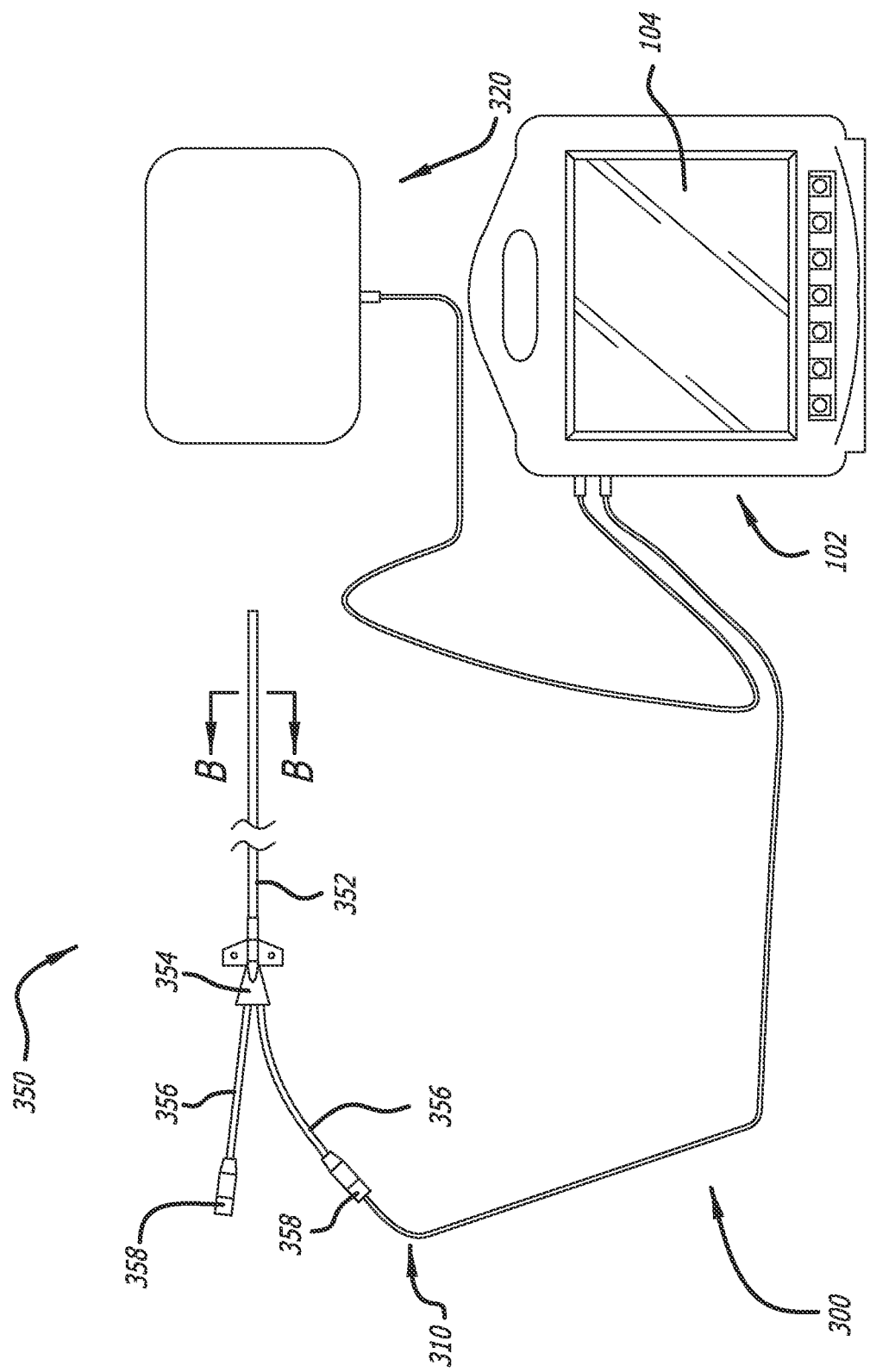
FIG. 3 displays an example optical catheter tip tracking system and a catheter, according to some embodiments.

FIG. 3 displays an example optical catheter tip tracking system 300 and a catheter 350, according to some embodiments. As shown, the optical tip-tracking system 300 includes a light-emitting stylet 310, a light detector 320, and a console 102 configured to operably connect to the light-emitting stylet 310 and the light detector 320. Optical tip-tracking system 300 also includes a display screen 104, which may be a standalone screen or be integrated into console 102. Optical tip-tracking system 300 can also include a medical device, such as the catheter 350 in this example.

In this example, the catheter 350 is a peripherally inserted central catheter (PICC). In another example catheter 350 can be a central venous catheter (CVC). A light-emitting stylet 310 including a light source, such as one or more LEDs in a distal-end portion (e.g., a tip) of the stylet 310, can be disposed in one or more lumens of catheter 350. Alternatively, the light-emitting stylet 310 can convey light (e.g., via an optical fiber), from an external source (e.g., a light within console 102) to emit light from the distal-end portion (e.g., the tip) of stylet 310.

In this example, catheter 350 is a diluminal catheter including a catheter tube 352, a bifurcated hub 354, two extension legs 356, and two Luer connectors 358. Alternatively, catheter 350 may be a monoluminal catheter, or a multi-luminal catheter with three or more lumens. In this example, two lumens extend through diluminal catheter 350, and are formed of adjoining lumen portions. Each of the two extension legs 356 has an extension-leg lumen fluidly connected to one of the two hub lumens. Either lumen extending through the catheter 350 can accommodate a light-emitting stylet 310 disposed therein.

The system 300 can further include light detector 320, which includes a plurality of photodetectors 122 disposed within the light detector 320, and configured to detect the light emitted from the light source of light-emitting stylet 310. The photodetectors 122 are arranged in an array such that the light emitted from light-emitting stylet 310 remains detectable by at least one of the photodetectors 122, even when the light is anatomically blocked (e.g., by a rib) from another one or more of the photodetectors 122.

Optical catheter tip tracking system 300 and light-emitting stylet 310 are described further in US 2021/0154440, which is incorporated by reference in its entirety into this application.

However, an additional problem commonly arising with ultrasound imaging is identifying the proper anatomical targets. For example, some challenges faced by clinicians while performing ultrasound-assisted catheter insertion include differentiating veins from arteries, finding a particular target artery or vein, such as the superior vena cava (SVC), and generally finding a suitable target blood vessel for catheter insertion. Locating the correct targets may consume clinical time and resources, and errors could cause potentially dangerous complications. The disclosed system and methods can address these issues by providing a target identification system along with an ultrasound probe and a needle guidance system. Accordingly, the disclosed system can simultaneously determine the location of anatomical targets and medical instruments in relation to the ultrasound probe. The disclosed embodiments can also be applied in other ultrasound-based procedures and therapies, for example for biopsy, nerve blocks, or drainage procedures.

Figure 4A:
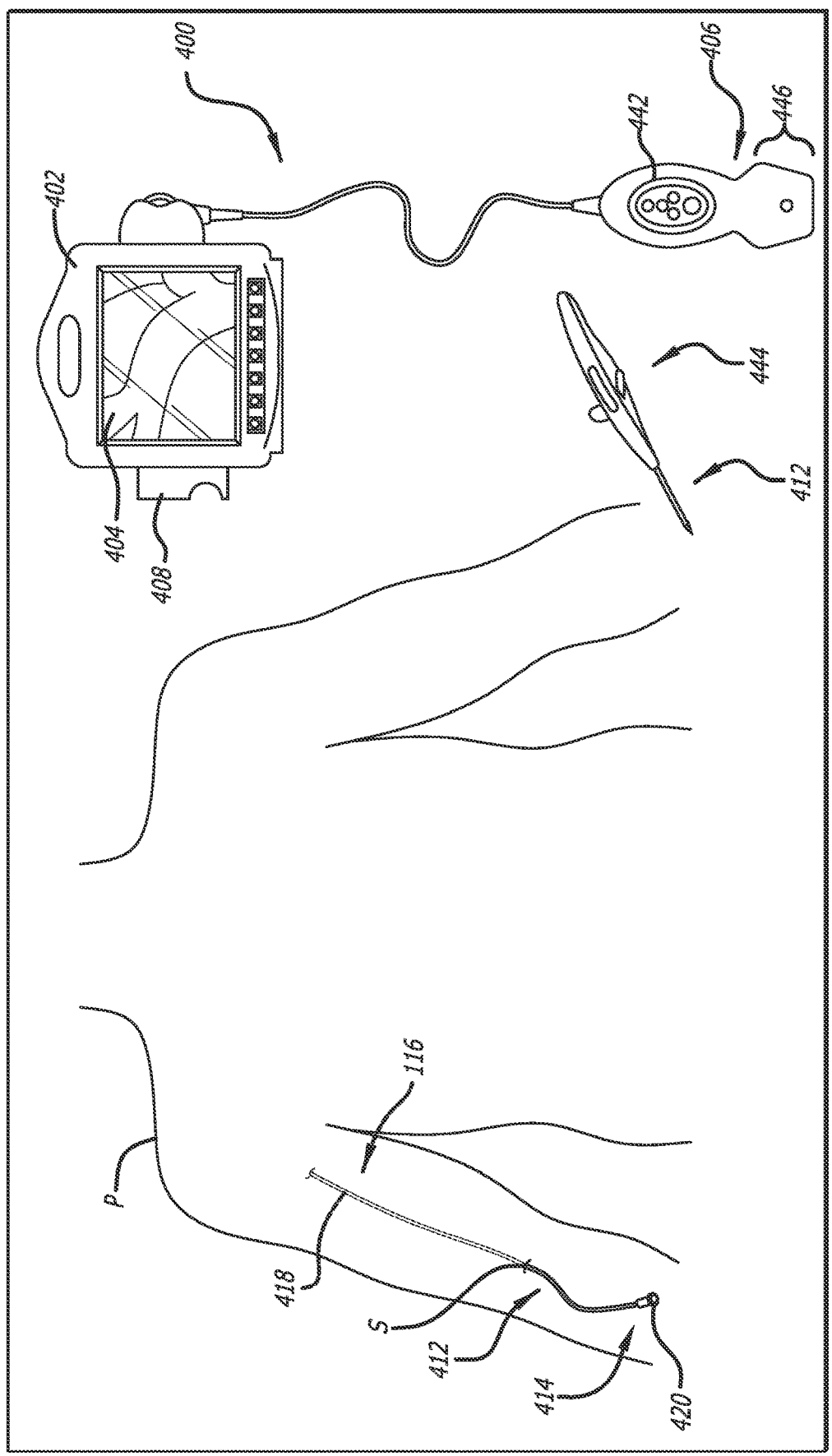
FIG. 4A illustrates an example ultrasound probe, target identification system, and needle guidance system with a patient, according to some embodiments.

FIG. 4A illustrates an example ultrasound probe 406, and a target identification and needle guidance system 400 with a patient, according to some embodiments. In this example, system 400 includes both target identification and needle guidance functionalities. In particular, system 400 can perform target identification based on artificial intelligence (AI) methods, which can be trained to recognize targets based on the ultrasound image.

For example, the system may recognize specific blood vessels or classes of blood vessels, or recognize targets in ultrasound-based biopsy, nerve block, or drainage procedures, based on AI. In the case of blood vessel targets, system 400 may be trained using ultrasound data from correctly-identified blood vessels, and may classify or segment blood vessels based on features such as shape (e.g., eccentricity, interior angles, or aspect ratio), size (e.g., minor or major axis length, diameter, or perimeter), number and complexity of branches, and the like. In an example, the training may proceed by iteratively minimizing an error or loss function for predicted compared to actual classifications in a training set, as a function of model weights. Hyperparameters of the model may further be tuned with respect to a validation data set, and the model may be further evaluated against a testing data set. The trained model may then be deployed for use in a clinical setting.

In a typical usage example, a medical practitioner may use ultrasound probe 406 and target identification and needle guidance system 400 while inserting a PICC into the superior vena cava of patient P. For example, the PICC can be advanced through patient P's right basilic vein, right axillary vein, right subclavian vein, right brachiocephalic vein, and into the superior vena cava. In this example, the system 400 can help the practitioner identify the superior vena cava in ultrasound images, while also helping guide the insertion needle toward the superior vena cava. In some embodiments, system 400 can additionally track the position of the PICC and confirm correct insertion of the PICC into the superior vena cava, as described herein below.

In an embodiment, the system 400 can assist the clinician to identify targets by providing the clinician with information characterizing potential targets, for example a predicted classification and a confidence level associated with the classification. Alternatively, system 400 can suggest one or more potential targets for the clinician's approval, or even select the target automatically.

The system can perform classification or segmentation of targets based on any AI or machine learning (ML) method, and is not limited by the present disclosure. In some embodiments, the AI or machine learning methods include supervised classification methods and/or image segmentation methods. For example, the system may use logistic regression or other linear classifiers, support vector machines, quadratic classifiers, kernel estimation, decision trees, neural networks, convolutional neural networks, or learning vector quantization. In a typical embodiment, system 400 uses a supervised learning method to perform image segmentation or classification of potential targets. For example, system 400 may identify specific targets, such as affirmatively identifying the superior vena cava or cavoatrial junction.

Alternatively, system 400 may provide a probability that a potential target is the user's desired target, such as an 80% or 90% probability that a particular blood vessel is the SVC. In another example, system 400 may classify targets more broadly, such as by identifying whether a blood vessel is a vein or artery.

The AI or machine learning methods may result in models that may be trained, as described above, before clinical usage based on a training set including ultrasound images of known targets. For example, the clinician may download training data and/or a trained and tuned model from a centralized repository. In such an example, the clinician may occasionally download new training data or a new trained model in order to recognize new targets or classes of targets, or to improve the recognition accuracy. Alternatively, the clinician can train system 400, for example by inputting information about the characteristics or identities of potential targets to system 400, or correcting any mistaken identifications of targets. In some embodiments, the system may alternatively use unsupervised learning methods to segment or classify potential targets, and is not limited by the present disclosure.

In addition to models that are only pre-trained (e.g., models trained prior to utilization), AI or machine learning methods may be utilized to generate models that may be dynamically trained, e.g., results of scoring of the model are utilized as training data.

By providing ultrasound-based target identification together with needle guidance, system 400 can provide accurate, safe, and expeditious methods for ensuring a needle is implanted in the intended target. System 400 can automate key steps of ultrasound-based therapies, such as identifying an anatomical target and advancing the needle during catheter insertion. This automation thereby reduces time and effort for clinicians, and may improve clinical accuracy and reduce the rate of errors and complications.

In addition, FIG. 4A shows the general relation of system 400 to the patient P during a procedure to place a catheter 412 into a vasculature of the patient P through a skin insertion site S. As in the example of FIG. 1 above, the catheter 412 includes proximal portion 414, which remains exterior to the patient, and distal portion 416, which resides within the vasculature after placement is complete. System 400 is employed to position a distal tip 418 of the catheter 412 in a desired position within the vasculature, with the aid of ultrasound imaging, magnetic needle guidance, and target identification.

Placement of a needle into a vasculature of a patient such as the patient P at the insertion site S is typically performed prior to insertion of the catheter 412. It should be appreciated the target identification and needle guidance system 400 has a variety of uses, including placement of needles in preparation for inserting the catheter 412 or other medical components into the body of patient P, such as X-ray or ultrasound markers, biopsy sheaths, nerve blocks, drainage, ablation components, bladder scanning components, vena cava filters, etc. For example, endoscopic ultrasound can be used to perform fine-needle aspiration biopsy, by guiding the placement of the biopsy needle. In this case, the disclosed ultrasound and target identification and needle guidance system 400 can be used to image and identify the target of the biopsy, and to guide the biopsy needle to the target. In another example, ultrasound can be used to guide needle placement in nerve block procedures. In this case, the disclosed system 400 can be used to image and identify the targeted nerve, and to guide the needle to the target. In a third example, ultrasound can be used to guide drainage procedures, e.g., to guide placement of a drainage catheter for draining collected fluid, such as from an abscess or a post-surgical collection of fluid. In this case, the disclosed system 400 can be used to image and identify the targeted abscess, and to guide the needle and/or catheter to the target.

Display screen 404 is integrated into the console 402 and is used to display information to the clinician, such as an ultrasound image of the targeted internal body portion obtained by the ultrasound probe 406. Indeed, the needle guidance process of target identification and needle guidance system 400 graphically guides insertion of a needle into a target (e.g., a blood vessel) of a patient by way of the display screen 404. In some examples, the display screen 404 may be separate from the console 402. In some embodiments, the display screen 404 is an LCD device.

In this example, display 404 shows the ultrasound image obtained by ultrasound probe 406. In particular, the image may include the insertion target of the needle, for example a target blood vessel for insertion of a PICC. System 400 can apply AI methods to identify this target by applying a supervised learning model to process features of the target in the ultrasound image, and thereby determine a classification of the target and an associated confidence score, as disclosed herein. In addition, the system can use magnetic needle guidance in concert with ultrasound, thereby informing the clinician when the needle reaches the vicinity of the target, for example by an ultrasound reflection or "flash" from the needle. This will be described further in the example of FIG. 4B below. In some embodiments, system 400 can further provide PICC tracking and PICC placement confirmation, as described in the examples of FIGS. 6A, 6B, and 7 below.

FIG. 4A additionally depicts a needle-based device, namely a catheter-insertion device 444, used to gain initial access to the vasculature of the patient P via the insertion site S to deploy the catheter 412. The needle of the catheter-insertion device 444 can cooperate with the needle guidance system 400 in enabling the needle guidance system 400 to detect the position, orientation, and advancement of the needle during an ultrasound-based placement procedure. Note that the needle of the catheter-insertion device 444 is merely one example of a needle or medical device that may be magnetized and used with the needle guidance system 400.

The needle magnetizer 408 is configured to magnetize all or a portion of a needle such as the needle of the catheter-insertion device 444 so as to enable the needle to be tracked during a placement procedure. The needle magnetizer 408 can include a single permanent magnet, a single electromagnet, a plurality of permanent magnets, a plurality of electromagnets, or a combination thereof within a body of needle magnetizer 408. For example, if a single permanent magnet, the permanent magnet can be a hollow cylindrical magnet disposed within the body of the needle magnetizer. If more than one permanent magnet, the permanent magnets can be disposed within the body of the needle magnetizer 408 in a multipole arrangement. Alternatively, the permanent magnets are annular magnets disposed within the body of the needle magnetizer in a stacked arrangement. In some embodiments, the needle magnetizer 408 can also be used to magnetize part or all of a catheter, such as the catheter's tip.

Figure 4B:
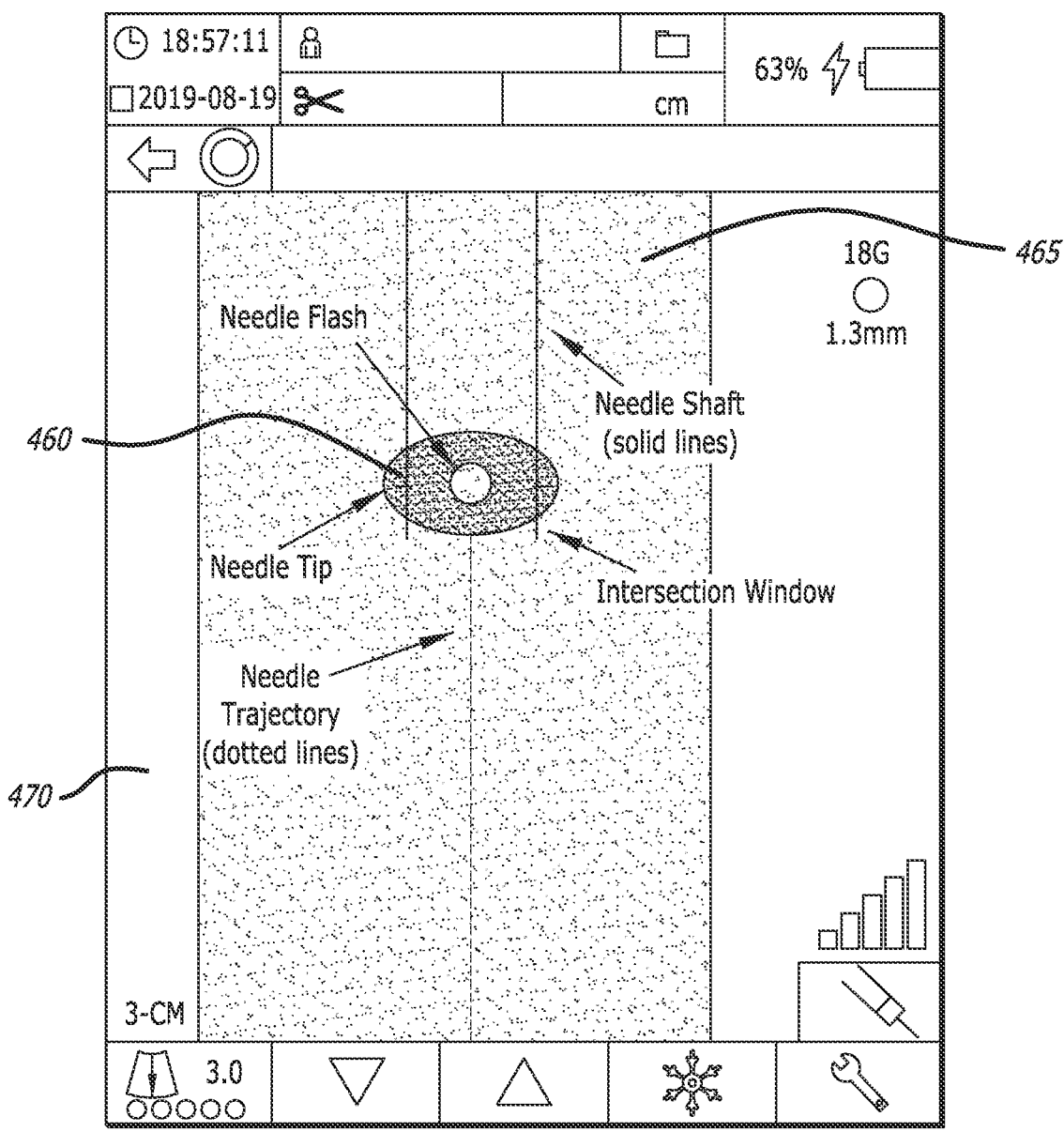
FIG. 4B illustrates an example console display of an ultrasound, needle guidance, and target identification system, according to some embodiments.

FIG. 4B illustrates an example console display 450 of an ultrasound, needle guidance, and target identification system, according to some embodiments. In this example, a clinician is inserting a needle into blood vessel 460, as shown in the ultrasound image 465 in console display 450. The ultrasound image 465 shows a depth-wise section of the patient's tissue, which is located under ultrasound probe 406 and corresponds to ultrasound beam 260 in the example of FIG. 2. The tissue section includes the target blood vessel 460. Depth scale 470 shows the advancing depth along the vertical dimension of the displayed tissue section. Display 450 also shows an outline of the needle shaft (solid lines), as the needle advances. The system can determine the location of the needle shaft via magnetic or optical needle tracking methods, as described herein. In addition, display 450 shows a projection of the needle's trajectory (dotted lines).

In this example, the system can apply artificial intelligence (AI) methods to identify target blood vessel 460. In a typical embodiment, the system uses a supervised learning method to segment or classify potential targets. For example, the system can use logistic regression or other linear classifiers, support vector machines, quadratic classifiers, kernel estimation, decision trees, neural networks, convolutional neural networks, or learning vector quantization. In some embodiments, the ultrasound image 465 can be filtered (e.g., by a linear filter such as a mean filter, or a non-linear filter such as an order statistic filter) in order to improve image quality. In some embodiments, segmentation of the image 465 into smaller blocks, or an active contour model can be applied. In some embodiments, pattern matching based on Markov random fields or neural networks can be applied.

In an embodiment, system 400 can classify potential targets based on an AI model. In applying the model, system 400 can evaluate the model based on features corresponding to observable properties of the potential targets, such as blood vessels, in image 465. For example, the features may include shape of a blood vessel (e.g., eccentricity, interior angles, or aspect ratio), size (e.g., minor or major axis length, diameter, or perimeter), number and complexity of branches, and the like. In an example, the model is a regression model, and system 400 evaluates the model as a probability function of the feature values, such as a weighted sum. In another example, the model is an artificial neural network such as a convolutional neural network, and system 400 evaluates the model by successively applying one or more hidden layers of neurons on the feature values. Each neuron can comprise a nonlinear activation function on its inputs. In particular, the first layer of neurons can apply nonlinear activation functions on all the feature values, and subsequent layers can apply nonlinear activation functions on all the outputs of the previous layers. Such an artificial neural network can adjust its weighted associations according to a learning rule based on an error value or another cost function. In the case of multiple hidden layers, system 400 can identify abstract features, based on the original set of input features, via deep learning.

Based on AI, the system may identify target 460, and/or may assist the clinician to identify targets by providing the clinician with identifying information characterizing potential targets. For example, the clinician may inform the system that the desired target is the patient's superior vena cava. In this example, the target identification logic may then determine that a particular blood vessel is the superior vena cava, and may accordingly flag this blood vessel for recommendation to the clinician as the insertion target. Alternatively, the target identification logic may automatically assume this identified blood vessel is the target, and may proceed to guide the clinician based on this assumption. In identifying a particular target, such as the SVC, the console may receive the ultrasound image 465, and may use image 465 as input into an AI-based model previously trained on ultrasound images of identified blood vessels. Evaluation of the AI-based model can result in a probability or confidence score that a blood vessel within the ultrasound image is the particular vessel requested by the user, e.g., the SVC.

In an alternative example, the clinician may not inform the system of a particular desired target. In this case, the target identification logic may then identify all potential targets present in the ultrasound image 465, and may flag all these potential targets for communication to the clinician. In an example, the target identification logic may rank the potential targets, for example by relevance or importance as an insertion target, by confidence of the classification, etc., and may communicate the recommendations to the clinician in the order of the ranking. In identifying all potential targets present in the ultrasound image 465, the console may receive image 465, and may use image 465 as input into an AI-based model trained with ultrasound images of identified blood vessels. The console can evaluate the AI-based model for each respective potential target in the received image 465, resulting in a respective probability or confidence score that each respective potential target is any of a set of known targets.

Once the potential targets have been identified and/or flagged for display, the console can direct the display 450 to output identifying information about these targets to the user. For example, display 450 may show a predicted classification of target 460, such as a blood vessel type, location, or name, and may show a confidence level associated with this classification. The predicted classification can be based on the AI model, e.g. by choosing the classification with the highest confidence score or a classification with a confidence score higher than a threshold value, such as 95%. Alternatively, system 400 can suggest one or more potential targets for the clinician's approval, or even select the target automatically. For example, if more than one potential target is present in the depth-wise section of the patient's tissue on display 450, system 400 can indicate the potential targets to the user, e.g. by highlighting them on display 450, or can provide the user with a menu of one or more suggested targets, or select the target automatically. Such suggestions can be based on the output of the AI model, for example based on having a high confidence score.

The system can display the predicted classification of target 460 and/or of a list of potential targets based on the probability or confidence score from evaluating the AI-based segmentation or classification model using image 465 as input. For example, if image 465 contains two potential targets, and the system has been trained to recognize 90 identified target blood vessels, the system can evaluate a classification probability for each of the two potential targets being each the 90 known targets.

In an example, the system may determine with high confidence that the first potential target is a particular blood vessel, such as the SVC, and may accordingly identify the first potential target as such via display 450. The system may identify the first potential target when the probability or confidence score from the AI-based model exceeds a threshold, for example greater than 97% confidence. In another example, the system may identify that the second potential target has a 75% chance of being the right renal vein, and a 25% chance of being the right suprarenal vein, and may accordingly display both of these probabilities via display 450. The system may display multiple probabilities when the scores from the AI-based model are lower than a threshold, for example lower than 97% confidence.

In some embodiments, the console can display the targets by overlaying a visual indicator (e.g., a circle or square, or another icon) on the target 460 in ultrasound image 465. In an embodiment, the display 450 can indicate whether the needle trajectory will intersect with the target 460, e.g. by highlighting the intersection. In some embodiments, the system can determine the target in part based on the needle's projected trajectory, for example the system may identify potential targets that are in, or close to, the needle's trajectory. For example, the AI model may incorporate one or more features measuring proximity of a potential target to the needle's trajectory. In this case, the AI model may be trained based on these proximity features, together with geometrical features of the potential targets. In an embodiment, the console can determine the distance from the needle's current location to the target, and display this distance. In an embodiment, the console can also estimate the time until the needle will advance to the target, and display this estimate. In various embodiments, the distance and/or time to the target can be estimated by a formula, and/or based on AI methods. For example, the system may be trained to estimate the time based on a training set of previous implantations.

Note that insertion can be performed out-of-plane (i.e., when the needle's trajectory is not in the plane of the ultrasound beam 260, as shown in the example of FIG. 2) or in-plane (i.e., when the needle's trajectory is in the plane of the ultrasound beam). During in-plane insertion, the solid lines show the outline of the needle's actual location. However, during out-of-plane insertion, because part or all of the needle may not actually be located in the plane of the ultrasound beam, the solid lines show a projection of the needle's outline into the plane of the beam. In both cases, the location of the needle may be determined via magnetic or optical needle tracking, as described herein, rather than directly from the ultrasound image. In the case of out-of-plane insertion, display 450 can also show an Intersection Window, which is the intersection between the needle shaft and the plane of the ultrasound beam.

During out-of-plane insertion, adjusting the angle of the needle up or down or changing the distance between the needle and probe may change the position of the Intersection Window. A flat angle is required for shallow insertion, while a steep angle is required for deeper insertion.

When the needle overlay advances through the Intersection Window, a needle flash appears in the Intersection Window. The needle flash is the reflection of the ultrasound energy from the needle. The presence of the needle flash is an indication the needle is at the target, because it shows the needle tip has reached the plane of the ultrasound beam.

In some embodiments, the system 100 of FIG. 1 may include an alternative-reality (AR) headset and corresponding AR anatomy representation logic. The AR anatomy representation logic may be configured to generate a virtual object that is presented in an AR environment such as a virtual reality, augmented reality or a mixed reality in which the virtual object overlays an image produced by the system 10 (e.g., an ultrasound image) or a series of images (e.g., a video) associated with a real-world setting (e.g., video including a patient or a body part of the patient, a physical structure, etc.). The virtual object may be visible through the AR headset or visible on a display of the console 102 without the AR headset. For example, the display 450 of FIG. 4B may be represented as a virtual object visible through the AR headset or visible on a display of the console 102. Alternatively, in lieu of the system 100 as described herein, it is contemplated that a magnetic field imaging system may be deployed. It is contemplated that components and functions of the console 102 described in reference to the system 100 should be understood to apply to the magnetic field imaging system or a similar system. Notwithstanding the foregoing, in some embodiments of the system 100, at least a portion of the functionality of the AR anatomy representation logic may be deployed within the AR headset in lieu of the console 102. Herein, the AR headset or another component operating in cooperation with the AR headset may serve as the console or performs the functions (e.g., processing) thereof.

With respect to "alternative reality," the term alternative reality may pertain to virtual reality, augmented reality, and mixed reality unless context suggests otherwise. "Virtual reality" includes virtual content in a virtual setting, which setting can be a fantasy or a real-world simulation. "Augmented reality" and "mixed reality" include virtual content in a real-world setting such as a real depiction of a portion of a patient's body including the anatomical element. Augmented reality includes the virtual content in the real-world setting, but the virtual content is not necessarily anchored in the real-world setting. For example, the virtual content can be information overlying the real-world setting. The information can change as the real-world setting changes due to time or environmental conditions in the real-world setting, or the information can change as a result of a consumer of the augmented reality moving through the real-world setting; however, the information remains overlying the real-world setting. Mixed reality includes the virtual content anchored in every dimension of the real-world setting. For example, the virtual content can be a virtual object anchored in the real-world setting. The virtual object can change as the real-world setting changes due to time or environmental conditions in the real-world setting, or the virtual object can change to accommodate the perspective of a consumer of the mixed reality as the consumer moves through the real-world setting. The virtual object can also change in accordance with any interactions with the consumer or another real-world or virtual agent. Unless the virtual object is moved to another location in the real-world setting by the consumer of the mixed reality, or some other real-world or virtual agent, the virtual object remains anchored in the real-world setting. Mixed reality does not exclude the foregoing information overlying the real-world setting described in reference to augmented reality.

An alternative-reality (AR) headset and corresponding AR anatomy representation logic are described further in U.S. patent application Ser. No. 17/397,486, filed Aug. 9, 2021, which is incorporated by reference in its entirety into this application.

Figure 5:
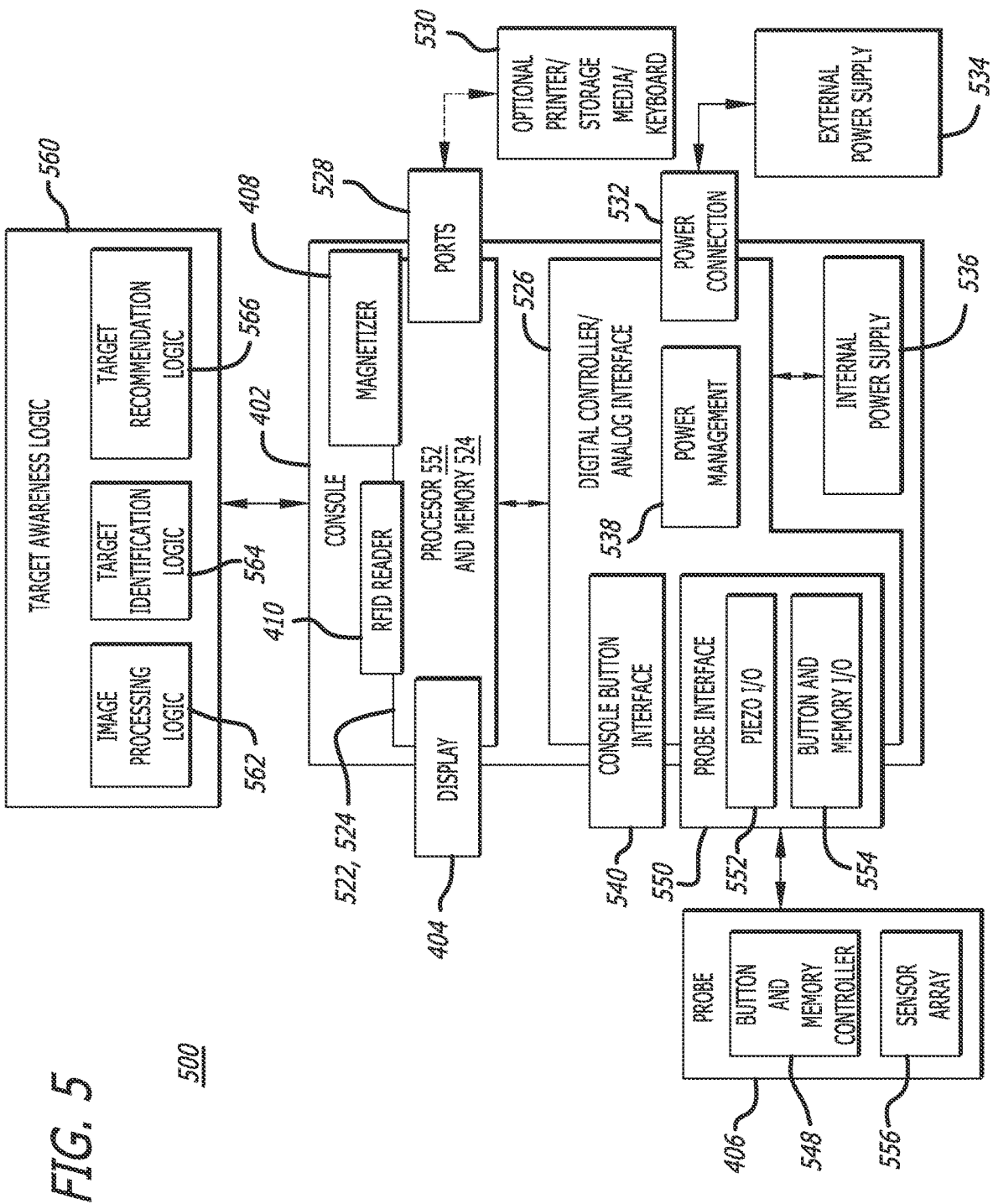
FIG. 5 shows a block diagram of a needle guidance and target identification system, in accordance with some embodiments.

FIG. 5 shows a block diagram of a needle guidance and target identification system 500, in accordance with some embodiments. A console button interface 540 and control buttons 142 (see FIG. 1) included on the ultrasound probe 406 can be used to immediately call up a desired mode to the display screen 404 by the clinician to assist in the placement procedure. As shown, the ultrasound probe 406 further includes a button and memory controller 548 for governing button and ultrasound probe operation. The button and memory controller 548 can include non-volatile memory (e.g., EEPROM). The button and memory controller 548 is in operable communication with a probe interface 550 of the console 402, which includes a piezo input/output component 552 for interfacing with the probe piezoelectric array and a button and memory input/output component 554 for interfacing with the button and memory controller 548.

The console 402 houses a variety of components of the needle guidance and target identification system 500, and console 402 may take a variety of forms. A processor 522, including memory 524 such as random-access memory ("RAM") and non-volatile memory (e.g., electrically erasable programmable read-only memory ("EEPROM")) is included in the console 402 for controlling system function and executing various algorithms during operation of the needle guidance and target identification system 500.

For example, the console 402 is configured with target awareness logic 560 to instantiate a target identification process for recognizing an anatomical target (e.g., a blood vessel such as the SVC) of a patient. The target identification process involves processing of ultrasound images by the console 402 with artificial intelligence methods to identify anatomical targets, as disclosed herein. In particular, the target awareness logic 560 can apply image processing logic 562 to receive the ultrasound images and locate potential targets within the images. It can then apply target identification logic 564 to identify the potential targets, for example by determining the identity of the individual potential targets, or by matching one potential target to a desired target. Target identification logic 564 may use a supervised learning heuristic, as described in the example of FIGS. 4A and 4B above. Finally, target awareness logic 560 can apply target recommendation logic 566 to suggest one or more targets to the user. For example, target recommendation logic 566 can provide the clinician with information identifying and/or characterizing potential targets, for example a predicted classification of a potential target and a confidence level associated with the classification. Alternatively, target recommendation logic 566 can suggest one or more potential targets for the clinician's approval, or even select a particular target automatically.

In addition, the console 402 is configured to instantiate a needle guidance process for guiding insertion of a needle into the anatomical target. The needle guidance process uses a combination of ultrasound-imaging data and magnetic-field data received by the console 402 for guiding the insertion of the needle into the target of the patient.

A digital controller/analog interface 526 is also included with the console 402 and is in communication with both the processor 522 and other system components to govern interfacing between the ultrasound probe 406, the needle magnetizer 408, and RFID-tag reader 410 and other system components.

The RFID reader 410 is configured to read at least passive RFID tags included with needles or other medical devices (e.g., catheter-insertion device 144, as shown in FIG. 1), which enables the needle guidance and target identification system 500 to customize its operation to particular needle or medical-device parameters (e.g., type, size, etc.). For example, the needle-guidance process, once instantiated by the needle guidance and target identification system 500, is configured to adjust needle-guidance parameters in accordance with electronically stored information read from an RFID tag for a needle. In order to read such an RFID tag, the RFID-tag reader is configured to emit interrogating radio waves into the RFID tag and read electronically stored information from the RFID tag.

The needle guidance and target identification system 500 further includes ports 528 for connection with additional components such as optional components 530 including a printer, storage media, keyboard, etc. The ports 528 in some embodiments are universal serial bus ("USB") ports, though other port types or a combination of port types can be used for this and the other interfaces connections described herein. A power connection 532 is included with the console 402 to enable operable connection to an external power supply 534. An internal power supply 536 (e.g., a battery) can also be employed either with or exclusive of the external power supply 534. Power management circuitry 538 is included with the digital controller/analog interface 526 of the console 402 to regulate power use and distribution.

In addition to tracking the location of the insertion needle, it also can be useful to track a medical device during insertion, such as the tip and/or stylet of a PICC, central venous catheter (CVC), or other catheter. For example, such tip tracking can improve the accuracy and efficiency of catheter placement, improve patient outcomes, and reduce the risk of complications or injuries.

Figure 6A:
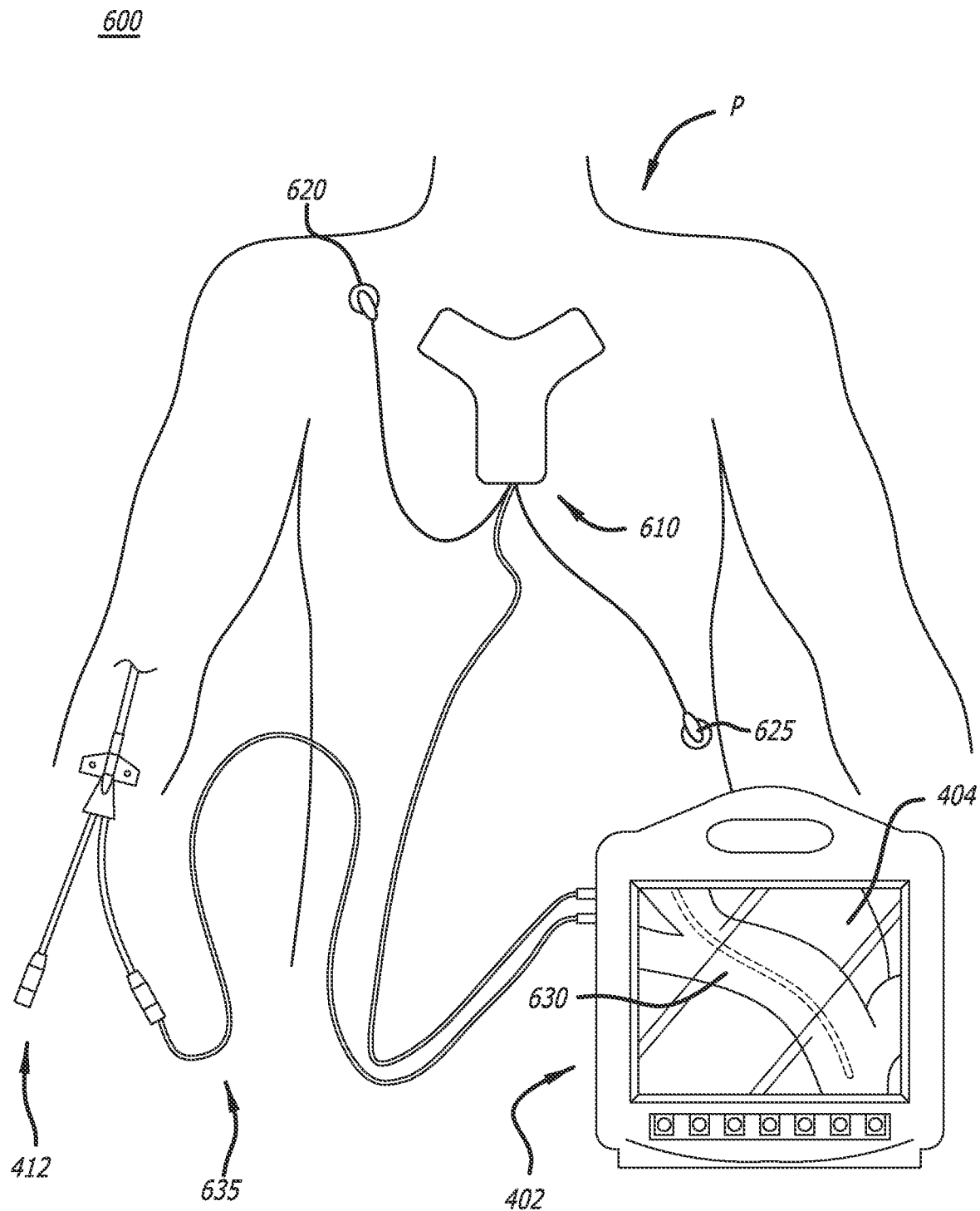
FIG. 6A illustrates a target identification system in use in conjunction with magnetic catheter tip tracking, in accordance with some embodiments.

FIG. 6A illustrates a target identification system 600 in use together with magnetic catheter tip tracking, in accordance with some embodiments. In some embodiments, the system 600 can use passive magnetic catheter tip tracking to locate and/or track tips of medical devices, such as PICCs, catheters, and/or stylets, and can thereby determine where such tips are located in relation to their target anatomical structures. In this example, PICC 412 is magnetically tracked by system 600 while being inserted into patient P. Alternatively, another catheter, or another medical instrument, may be tracked. Operational details of the magnetic tip tracking may function similarly to magnetic needle guidance, as in the example of FIG. 4B above. In particular, PICC 412, or the tip of stylet 635 disposed within PICC 412, can be magnetized. Sensor 610, which can be positioned on the chest of patient P, can detect the magnetic field from PICC 412.

In this example, sensor 610 of the tip-tracking system can detect the location of PICC 412, and can send signals representing the location of PICC 412 to console 402 to display on screen 404. In conjunction with the tip-tracking system, console 402 can also apply AI to recognize targets, such as target blood vessels. Display screen 404 can display an ultrasound image of target blood vessel 630 together with the location of PICC 412 and/or the insertion needle.

Initially the tip of PICC 412, or the tip of stylet 635 disposed within PICC 412, may be outside the range of sensor 610. As the stylet tip approaches the sensor 610, the console can display the location, orientation, and depth of the stylet 635 in relation to the sensor 610. The PICC 412 must be advanced slowly (e.g., 1 cm per second) and steadily in order to be tracked accurately. A clinician can continue to advance PICC 412 slowly until PICC 412 is inserted to the external measurements as required.

FIG. 6A also shows electrocardiography (ECG) probes 620 and 625. In an embodiment, during or following insertion of PICC 412 into the target blood vessel (or other target anatomical structure), the system can also be used to perform catheter tip confirmation based on ECG. Tip confirmation can confirm that the catheter tip has been inserted properly into the target. This will be discussed in the example of FIG. 7 below.

Fluoroscopic methods and confirmation of guidance for medical devices, such as guidewires and catheters, typically can expose clinicians and patients to potentially harmful X-ray radiation and contrast media. The disclosed magnetic methods for tip tracking in this example, optical methods (see FIG. 6B) for tip tracking, and ECG methods for tip confirmation (see FIG. 7) can accurately locate and confirm medical devices like guidewires and catheters without such exposure. Accordingly, by providing ultrasound-based target identification, needle guidance, and catheter tip tracking, system 600 provides safe and efficient methods for ensuring PICC 412 is correctly inserted in its intended target. The combination of target identification, needle guidance, and magnetic or optical catheter tracking can reduce clinical time and effort, and may improve patient outcomes.

Figure 6B:
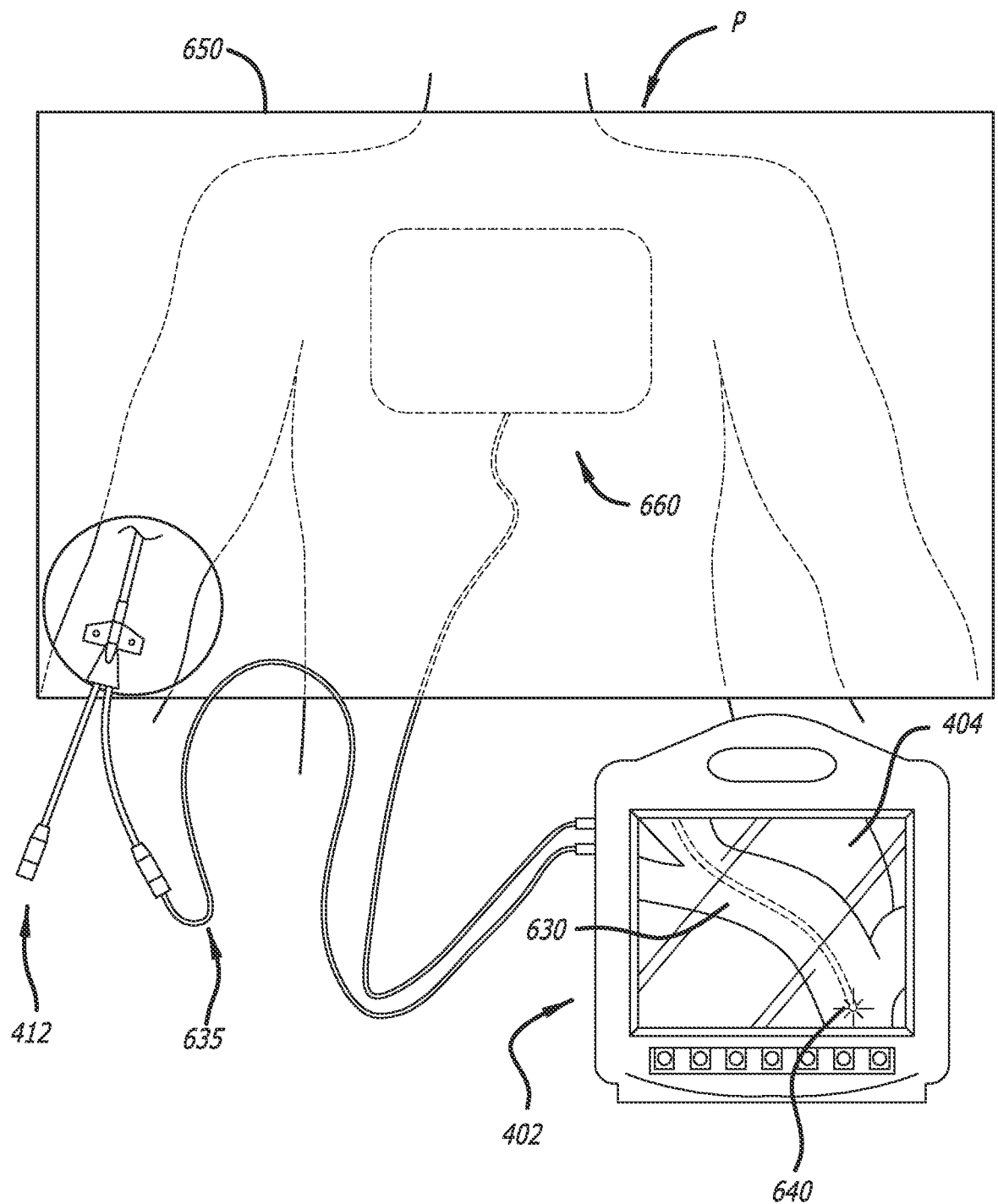
FIG. 6B illustrates a target identification system in use in conjunction with optical catheter tip tracking, in accordance with some embodiments.

FIG. 6B illustrates a target identification system in use together with optical catheter tip tracking, in accordance with some embodiments. In some cases, magnetic and electromagnetic means for tracking the tips of the medical devices are prone to interference. Accordingly, optical tip-tracking methods, such as in the example of FIG. 3 above, can also be used in conjunction with the disclosed system and methods. As for the case of magnetic catheter tracking, the combination of target identification, needle guidance, and optical catheter tracking can reduce clinical time and effort, and improve outcomes.

In this example, light detector 660 of the optical tip-tracking system can detect the location of light-emitting stylet 635, and send a signal representing the location of light-emitting stylet 635 to console 402 to display on screen 404. In conjunction with the optical tip-tracking system, console 402 can also apply AI to recognize targets, such as target blood vessels. Accordingly, display screen 404 displays an ultrasound image of target blood vessel 630 together with the location 640 of light-emitting stylet 635.

A clinician can place light detector 660 of the optical tip-tracking system over the patient P, for example, over the patient's chest, as shown. A sterile drape 801 can also be draped over both the patient P and the light detector 660. The clinician can pierce the sterile drape 801 with a drape-piercing connector of the light-emitting stylet 635. The clinician can advance the catheter 412 from an insertion site to a destination within a vasculature of the patient P while emitting light from the light source (e.g., one or more LEDs) and detecting the light with photodetectors of light detector 660. The light source of stylet 635 may distally extend beyond a distal end of the catheter 412.

When the catheter 412 is a PICC, the PICC can be advanced with the light-emitting stylet 635 disposed therein through a right basilic vein, a right axillary vein, a right subclavian vein, a right brachiocephalic vein, and into an SVC of patient P. When the catheter 412 is a CVC, the CVC can be advanced with stylet 635 disposed therein through a right internal jugular vein, a right brachiocephalic vein, and into an SVC. The clinician can view the display screen 404 of the optical tip-tracking system while the display screen 404 graphically tracks the distal-end portion of the light-emitting stylet 635 through the vasculature of the patient P. The clinician can cease to advance the catheter 412 through the vasculature of the patient P after determining the distal-end portion of light-emitting stylet 635 is located at the destination by way of the display screen 404. In particular, the clinician can recognize the destination with the aid of the target identification system. For example, the target identification system can provide the clinician with information identifying and/or characterizing potential targets, for example a predicted classification of target blood vessel 630 and a confidence level associated with the classification. Alternatively, system 400 can suggest one or more potential targets for the clinician's approval, or even select the target (such as target blood vessel 630) automatically.

Figure 7:
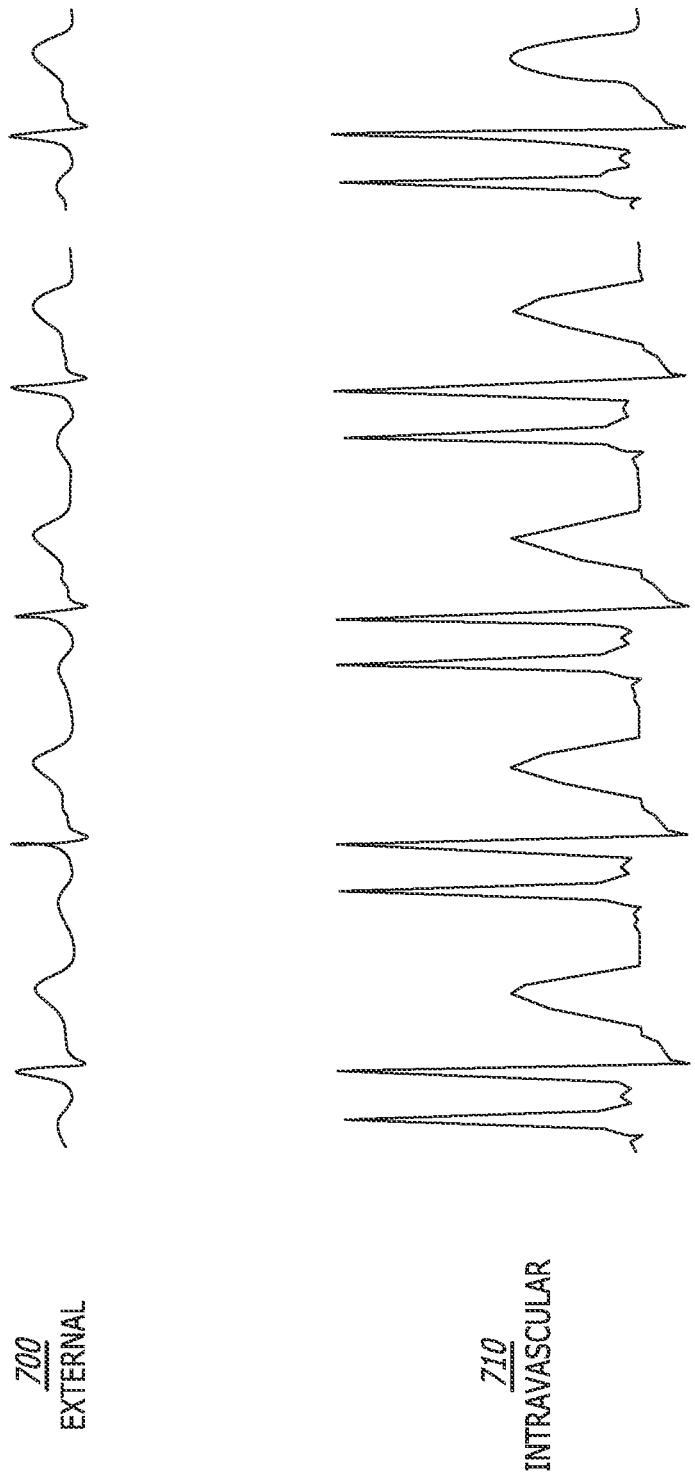
FIG. 7 shows catheter tip confirmation, in accordance with some embodiments.

FIG. 7 shows catheter tip confirmation based on electrocardiography (ECG), in accordance with some embodiments. In some embodiments, the system can use changes in an adult patient's measured ECG signal as an alternative to methods of PICC tip placement confirmation, like chest X-ray and fluoroscopy. In particular, ECG-based tip confirmation can accurately confirm the proper implantation of a catheter or PICC in a target in proximity to the cavoatrial junction, providing high confidence that the catheter or PICC is placed within 1 cm of the cavoatrial junction. ECG-based tip confirmation also reduces the exposure of both patient P and the clinician to harmful radiation, such as X-rays, and reduces clinical costs and time associated with taking such images. Moreover, clinicians can use ultrasound probe 406 for vessel access during insertion, and then easily transition to ECG to confirm catheter placement without the need for additional equipment. Because delays in therapy may negatively impact clinical care, the disclosed system potentially improves patient outcomes by expeditiously readying patients for treatment. Accordingly, the combination of target identification, needle guidance, and catheter placement confirmation can reduce clinical time and effort, as well as improving patient outcomes.

The cavoatrial junction is the point at which the superior vena cava meets the right atrium. At this intersection, blood volume and turbulence are high, which creates a favorable location for medicinal delivery to the body. Accordingly, by helping to position the PICC tip in proximity to the cavoatrial junction, the system can facilitate compliance with guidelines for proper PICC placement, which recommend placing PICC tips at the lower third of the superior vena cava, close to the cavoatrial junction. In patients where alterations of cardiac rhythm change the presentation of the P-wave, (e.g., in atrial fibrillation, atrial flutter, severe tachycardia, and pacemaker driven rhythm), an additional confirmation method may be required.

ECG probes 620 and 625 can be respectively placed on the patient's lower right shoulder and lower left side along the mid-axillary line (see FIG. 6A), with good skin-electrode contact. The system can display an ECG signal, such as signals 700 and 710 in this example, which is detected by intravascular electrodes and the body electrodes, such as ECG probes 620 and 625 in the example of FIG. 6A above. In various embodiments, the system may display signals 700 and 710 on display 404 of console 402, or on another display. In an embodiment, display 404 can provide simultaneous views of both catheter tip tracking and ECG signals 700 and 710. In an embodiment, the system displays two distinct ECG waveforms: waveform 700 is an external rhythm that establishes the baseline ECG, and waveform 710 is an intravascular waveform that shows changes in P-wave amplitude as the catheter tip approaches the cavoatrial junction.

In patients with a distinct P-wave ECG signal, the P-wave will increase in amplitude as the catheter approaches the cavoatrial junction. In an embodiment, the system can highlight the P-wave on the displayed signals. As the catheter advances into the right atrium, the P-wave in displayed signal 710 will decrease in amplitude and may become biphasic or inverted.

The clinician can observe the P-wave in order to confirm that the PICC has been properly placed. Both waveforms 700 and 710 can be frozen on the display 404 reference screen to compare changes in P-wave magnitude over time. To document proper catheter placement, the clinician can print or save a procedural record on the system.

Figure 8:
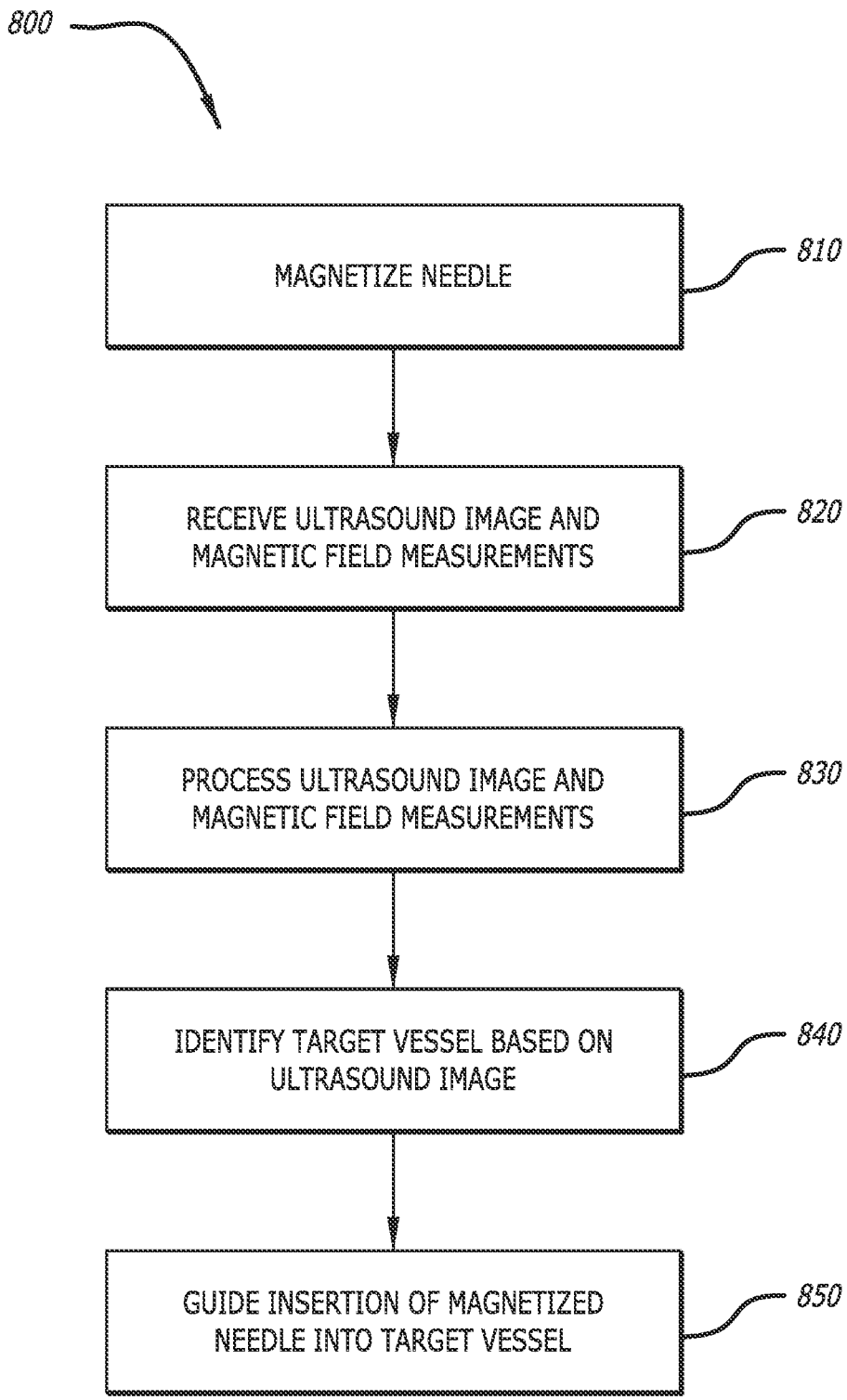
FIG. 8 shows a flowchart of an example method for ultrasound imaging, target identification, and needle guidance, according to some embodiments.

FIG. 8 shows a flowchart of an example method 800 for ultrasound imaging, target identification, and needle guidance, according to some embodiments. Each block illustrated in FIG. 8 represents an operation performed in the method 800 of ultrasound imaging, target identification, and needle guidance. The method can be performed by a target identification and needle guidance system, such as target identification and needle guidance system 400 in the examples of FIGS. 4A and 5 above. In an embodiment, the method can be performed by a console of such a system, such as console 402 in the examples of FIGS. 4A and 5 above.

As an initial step in the method 800, the needle can be magnetized (block 810). For example, a needle magnetizer such as needle magnetizer 408 may be configured to magnetize all or a portion of a needle such as the needle of the catheter-insertion device so as to enable the needle to be tracked during a placement procedure. The needle magnetizer can include a single permanent magnet, a single electromagnet, a plurality of permanent magnets, a plurality of electromagnets, or a combination thereof within a body of needle magnetizer.

Next, the console receives an ultrasound image and magnetic field measurements associated with the needle (block 820). The console can receive the ultrasound image from an ultrasound probe, such as ultrasound probe 406 in the example of FIG. 4A above. The console can receive the magnetic field measurements from magnetic sensors, such as magnetic sensors 258 in the example of FIG. 2 above.

Next, the console can process the ultrasound image and magnetic field measurements to determine the needle's position and orientation, and to identify the target (block 830). Based on the processed magnetic field measurements, the console can display the location, orientation, and depth of the needle in relation to the ultrasound probe. Processing the ultrasound image to identify the target will be described further in FIG. 9 below.

Next, the console can identify a target based on the ultrasound image (block 840). In a typical example, the target may be a target blood vessel for the eventual implantation of a medical device, such as a PICC or other catheter. However, any other type of target is possible, and is not limited by the present disclosure. In some embodiments, any of the AI-methods disclosed herein may be utilized to identify a target. As one example, any of the AI-methods disclosed herein may be utilized to identify a target insertion vessel (e.g., a vein) immediately prior to insertion of the needle into a patient. In such an example, the method 900 of FIG. 9 may be utilized. In an alternative example, any of the AI-methods disclosed herein may be utilized to identify a target during advancement of the needle within a patient's vasculature. For example, the ultrasound probe 406 may be utilized to obtain ultrasound images with the intention that the images track the advancement of the needle through the vasculature, e.g., along the arm of patient P as seen in FIG. 4A. Upon receipt of the ultrasound images, the target awareness logic 560, processing on the console 402, may analyze the ultrasound images using an AI-based model trained to identify particular targets, such as the SVC. Thus, as the console 402 continues to receive ultrasound images from the probe 406, the display 404 may provide a graphic indicating a confidence that the SVC is present within the ultrasound image rendered on the display 404. As an example, the target awareness logic 560, and particularly the target identification logic 564, may identify the SVC within an ultrasound image with at least a certain confidence score that was derived via processing of an AI-based model (e.g., by providing the ultrasound image as an input to the model) and, in response, generate an alert to the clinician that is rendered on the display 404 and/or render an indicator around the entry to the SVC. For example, such a rendering may include an intersection window around the entry to the SVC, similar to the intersection window illustrated in FIG. 4B.

Finally, the console can guide insertion of the magnetized needle into the target vessel (block 850). For example, the console can continue to update the displayed location, orientation, and depth of the needle as the clinician continues to advance the needle toward the target. The console can also continue to update the displayed ultrasound image of the patient's tissue containing the target. The console can also continue to display and identify the target via any of the AI-methods disclosed herein. In some embodiments, the console may also display a magnetically and/or optically tracked location of the catheter tip, such as a PICC tip, while the clinician advances the catheter. Finally, in some embodiments, the console can receive and display an ECG signal from ECG probes, which can enable the clinician to confirm correct insertion of the catheter.

Figure 9:
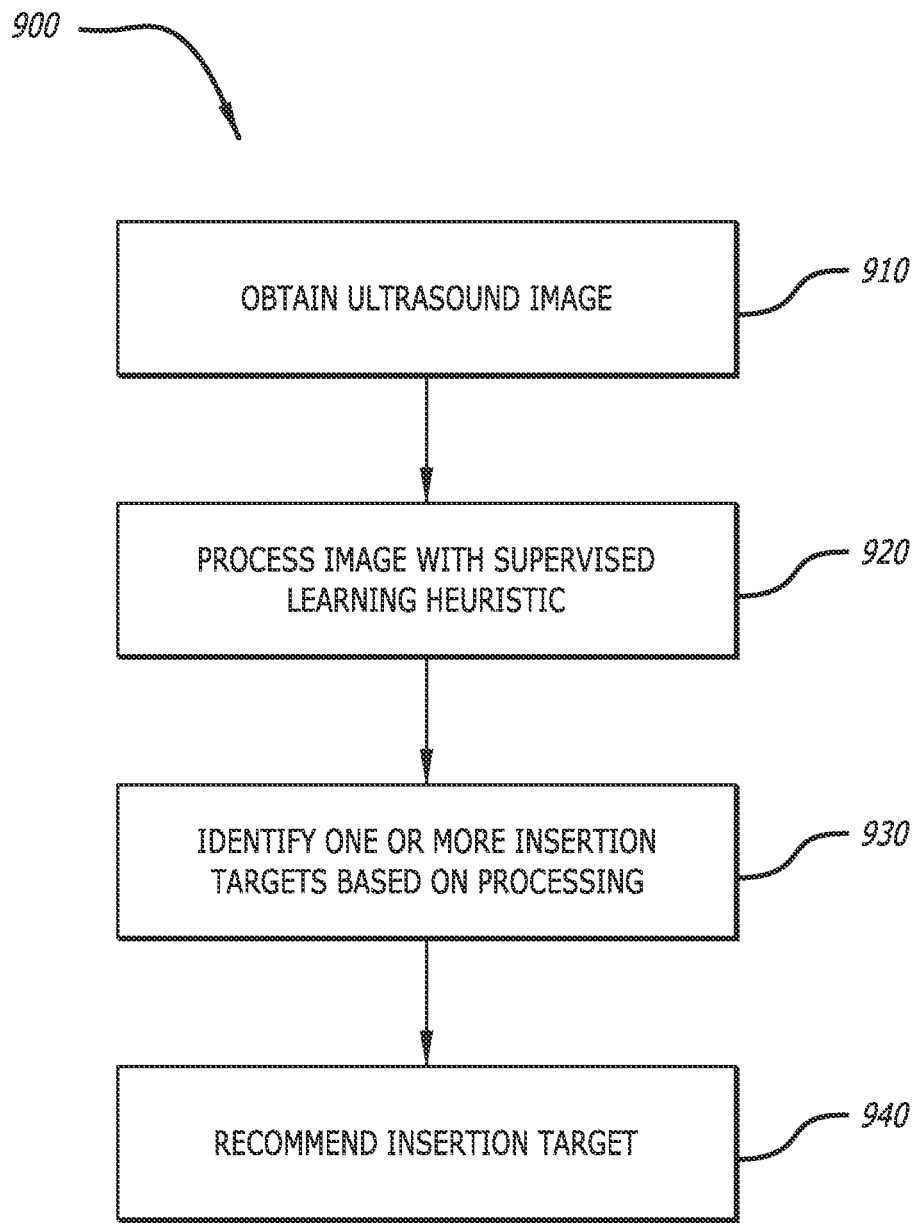
FIG. 9 shows a flowchart of an example method for target identification, according to some embodiments.

FIG. 9 shows a flowchart of an example method 900 for target identification, according to some embodiments. Each block illustrated in FIG. 9 represents an operation performed in the method 900 of target identification. In various embodiments, method 900 can be performed by a target identification and needle guidance system, such as target identification and needle guidance system 400 in the examples of FIGS. 4A and 5 above, by a console of such a system, such as console 402 in the examples of FIGS. 4A and 5 above, and/or by a target awareness logic, such as target awareness logic 560 in the example of FIG. 5 above.

As an initial step in the method 900, the console and/or target awareness logic can obtain an ultrasound image (block 910). In an embodiment, the console and/or target awareness logic can receive the ultrasound image from an ultrasound probe, such as ultrasound probe 406 in the example of FIG. 4A above.

Next, the image processing logic of the target awareness logic can process the image with a supervised learning heuristic (block 920). The image processing logic can apply a supervised learning method to segment or classify potential targets within the ultrasound image data. For example, the image processing logic can use logistic regression or other linear classifiers, support vector machines, quadratic classifiers, kernel estimation, decision trees, neural networks, convolutional neural networks, or learning vector quantization. In the cases of logistic regression or other linear classifiers, the model may determine a predicted probability as a weighted sum of feature values. For a neural network or other deep learning process, the model may transform the features via one or more layers of non-linear functions, such as artificial neurons, to determine a final predicted probability.

In an example where the targets are blood vessels, the system may be trained using ultrasound data from correctly-identified blood vessels, and may classify or segment blood vessels based on features such as shape (e.g., eccentricity, interior angles, or aspect ratio), size (e.g., minor or major axis length, diameter, or perimeter), number and complexity of branches, and the like. In an embodiment, the training may proceed by iteratively minimizing an error or loss function as a function of model weights, for predicted classifications compared to actual classifications in a training data set. Hyper-parameters of the model may further be tuned with respect to a validation data set, and the model may be further evaluated against a testing data set. The trained model may then be deployed for use in a clinical setting.

Next, the target identification logic of the target awareness logic can identify one or more insertion targets based on the processing (block 930). Based on the classification or segmentation from AI, the target identification logic may determine the specific identify of one or more potential targets. For example, the clinician may inform the system that the desired target is the patient's superior vena cava. In this example, the target identification logic may then determine that a particular blood vessel is the superior vena cava, and may accordingly flag this blood vessel for recommendation to the clinician as the insertion target. Alternatively, the target identification logic may automatically assume this identified blood vessel is the target, and may proceed to guide the clinician based on this assumption.

In another alternative example, the clinician may not inform the system of a particular desired target. In this alternative example, the target identification logic may then identify all potential targets present in the ultrasound image, and may flag all these potential targets for communication to the clinician. In an example, the target identification logic may rank the potential targets, for example by relevance or importance as an insertion target, by confidence of the classification, etc., and may communicate the recommendations to the clinician in the order of the ranking. In a final example, the target identification logic may simply attempt to identify all blood vessels, and inform the clinician of the best estimate classification of each blood vessel, as well as any other possible classifications and the confidence level of each classification.

Finally, the target recommendation logic of the target awareness logic can recommend an insertion target (block 940). Based on AI, the target recommendation logic may identify the target to the clinician, and/or may assist the clinician to identify targets by providing the clinician with information about potential targets. For example, the console display may show a predicted classification of the target, such as a blood vessel type, location, or name, and may show a confidence level associated with this classification. Alternatively, the console can suggest one or more potential targets for the clinician's approval, or even select the target automatically. For example, if more than one potential target is present in the ultrasound image, the console can indicate a set of potential targets to the user, e.g. by highlighting them on the display. Alternatively, the console can provide the user with a menu of one or more suggested targets, or select the target automatically.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A target recognition and needle guidance system, comprising:
   a console including a processor and non-transitory, computer-readable medium having stored thereon logic that, when executed by the processor, is configured to initiate:
      a target recognition process configured to (1) receive user input indicating a desired target, and (ii) identify a blood vessel of a patient corresponding to the desired target by applying a machine learning model to features of candidate targets in ultrasound-imaging data, wherein the blood vessel identified as the desired target is associated with a highest confidence score determined by the machine learning model, and
      a needle guidance process for guiding insertion of a needle into the blood vessel identified as the desired target by the machine learning model, wherein the machine learning model determines a proximity of a trajectory of the needle to the blood vessel identified as the desired target based on magnetic information about the needle, and wherein a catheter is implanted into the blood vessel identified as the desired target following the insertion of the needle; and an ultrasound probe configured to provide to the console electrical signals corresponding to the ultrasound-imaging data, the ultrasound probe including:
an array of transducers configured to convert reflected ultrasound signals from the patient into an ultrasound-imaging portion of the electrical signals, and
a magnetic sensor configured to provide to the console second electrical signals corresponding to the magnetic information about the needle.

2. The target recognition and needle guidance system of claim 1, wherein the machine learning model includes a supervised learning model trained based on previously-identified training targets.

3. The target recognition and needle guidance system of claim 1, wherein each of the candidate targets in the ultrasound-imaging data is associated with a confidence score determined by the machine learning model.

4. The target recognition and needle guidance system of claim 1, wherein the machine learning model includes one or more of the following supervised learning models:
logistic regression,
other linear classifiers,
support vector machines,
quadratic classifiers,
kernel estimation,
decision trees,
neural networks, or
learning vector quantization.

5. The target recognition and needle guidance system of claim 4, wherein the machine learning model includes the logistic regression, and wherein a confidence score of a first candidate target is determined as a weighted sum of the features of the candidate targets.

6. The target recognition and needle guidance system of claim 4, wherein the machine learning model includes the neural networks, and wherein a confidence score of a first candidate target is determined based on one or more non-linear activation functions of the features of the candidate targets.

7. The target recognition and needle guidance system of claim 2, wherein the supervised learning model is trained by iteratively minimizing an error, for classifications predicted by a candidate model compared to actual classifications of the previously-identified training targets.

8. The target recognition and needle guidance system of claim 1, wherein the blood vessel comprises a superior vena cava.

9. The target recognition and needle guidance system of claim 1, wherein the ultrasound probe provides a first ultrasound image prior to insertion of the needle, and wherein the machine learning model is based in part on the trajectory of the needle.

10. The target recognition and needle guidance system of claim 1, wherein the features of the candidate targets include one or more of the following features:
a shape of a candidate blood vessel of the candidate targets in the ultrasound-imaging data,
a size of the candidate blood vessel,
a number of branches of the candidate blood vessel, or
a complexity of branches of the candidate blood vessel.

11. The target recognition and needle guidance system of claim 1, wherein:
recognizing the blood vessel identified as the desired target comprises providing identifying information characterizing one or more candidate targets to a user, wherein the identifying information comprises a predicted classification of one or more potential targets and a confidence level associated with the predicted classification.

12. The target recognition and needle guidance system of claim 1, further comprising a display screen configured for graphically guiding the insertion of the needle into the blood vessel identified as the desired target.

13. The target recognition and needle guidance system of claim 1, further comprising:
one or more electrocardiogramabes configured to provide to the console electrical signals corresponding to electrocardiogramnformation,
wherein the logic, when executed by the processor, is further configured to initiate a catheter tip placement confirmation process based on the electrocardiogramnformation.

14. The target recognition and needle guidance system of claim 1, further comprising:
a needle magnetizer incorporated into the console configured to magnetize the needle.

15. The target recognition and needle guidance system of claim 14, wherein the needle guidance process for guiding insertion of the magnetized needle into the blood vessel identified as the desired target uses a combination of the ultrasound-imaging data and magnetic-field data received by the console.

16. The target recognition and needle guidance system of claim 15, wherein the ultrasound probe is configured to provide to the console the magnetic-field data, the ultrasound probe further including an array of magnetic sensors configured to convert magnetic signals from the magnetized needle into a magnetic-field portion of the electrical signals.

17. A target recognition and needle guidance system, comprising: a console including a processor and non-transitory, computer-readable medium having stored thereon logic that, when executed by the processor, is configured to initiate: a target recognition process configured to (1) receive user input indicating a desired target, and (ii) identify a blood vessel of a patient corresponding to the desired target by applying a machine learning model to features of candidate targets in ultrasound-imaging data, wherein the blood vessel identified as the desired target is associated with a highest confidence score determined by the machine learning model, and a needle guidance process for guiding insertion of a needle into the blood vessel identified as the desired target by the machine learning model, and wherein a catheter is implanted into the blood vessel identified as the desired target following the insertion of the needle, wherein the machine learning model determines a proximity of a trajectory of the needle to the blood vessel identified as the desired target based on optical information about the catheter; an ultrasound probe configured to provide to the console electrical signals corresponding to the ultrasound-imaging data, the ultrasound probe including: an array of transducers configured to convert reflected ultrasound signals from the patient into an ultrasound-imaging portion of the electrical signals; and a magnetic sensor configured to provide to the console second electrical signals corresponding to the optical information about the catheter.

* * * * *

UNITED STATES PATENT AND TRADEMARK OFFICE
CERTIFICATE OF CORRECTION

Page 1 of 1

PATENT NO. : 12,213,746 B2
APPLICATION NO. : 17/534099
DATED : February 4, 2025
INVENTOR(S) : Shayne Messerly et al.

It is certified that error appears in the above-identified patent and that said Letters Patent is hereby corrected as shown below:

In the Claims

Column 24, Line 12: Replace "electrocardiogramabes" with "electrocardiogram probes"

Column 24, Lines 13-14: Replace "electrocardiogramnformation" with "electrocardiogram information"

Column 24, Lines 17-18: Replace "electrocardiogramnformation" with "electrocardiogram information"

Column 24, Line 35: Insert --second-- before "electrical signals"

Column 24, Line 60: Replace "magnetic sensor" with "catheter light detector"

Signed and Sealed this
Third Day of February, 2026

John A. Squires
*Director of the United States Patent and Trademark Office*